United States Patent
Kania et al.

(10) Patent No.: US 9,593,054 B2
(45) Date of Patent: Mar. 14, 2017

(54) PRODUCTION OF DISTILLATE FUELS FROM BIOMASS-DERIVED POLYOXYGENATES

(71) Applicant: Virent, Inc., Madison, WI (US)

(72) Inventors: John Kania, Madison, WI (US); Paul Blommel, Oregon, WI (US); Elizabeth Woods, Middleton, WI (US); Brice Dally, Madison, WI (US); Warren Lyman, Madison, WI (US); Randy Cortright, Madison, WI (US)

(73) Assignee: Virent, Inc., Madison, WI (US)

( * ) Notice: Subject to any disclaimer, the term of this patent is extended or adjusted under 35 U.S.C. 154(b) by 0 days.

(21) Appl. No.: 13/832,376

(22) Filed: Mar. 15, 2013

(65) Prior Publication Data
US 2013/0263498 A1 Oct. 10, 2013

Related U.S. Application Data

(63) Continuation-in-part of application No. 13/368,023, filed on Feb. 7, 2012.
(Continued)

(51) Int. Cl.
*C07C 1/24* (2006.01)
*C10G 45/08* (2006.01)
(Continued)

(52) U.S. Cl.
CPC .................. *C07C 1/24* (2013.01); *C10G 3/45* (2013.01); *C10G 3/46* (2013.01); *C10G 3/47* (2013.01); *C10G 3/48* (2013.01); *C10G 3/49* (2013.01); *C10G 3/50* (2013.01); *C10G 3/52* (2013.01); *C10G 45/08* (2013.01); *C10G 45/10* (2013.01); *C10L 1/04* (2013.01); *C10L 1/08* (2013.01); *C10G 2300/1011* (2013.01); (Continued)

(58) Field of Classification Search
CPC ... C10G 3/45–3/50; C10G 3/52; C10G 45/08; C10G 45/10; C10L 1/04; C10L 1/08
See application file for complete search history.

(56) References Cited

U.S. PATENT DOCUMENTS

| 6,699,457 B2 | 3/2004 | Cortright et al. |
| 6,953,873 B2 | 10/2005 | Cortright et al. |

(Continued)

FOREIGN PATENT DOCUMENTS

WO 2008109877 A1 9/2008

OTHER PUBLICATIONS

Blommel, et al., Production of Conventional Liquid Fuels from Sugars, Aug. 25, 2008, www.virent.com/BioForming/Virent_Technology_Whitepaper.pdf, XP-002631372, 14 pages.
(Continued)

*Primary Examiner* — Brian McCaig
(74) *Attorney, Agent, or Firm* — Quarles & Brady LLP

(57) ABSTRACT

The present invention provides methods, reactor systems and catalysts for converting biomass and biomass-derived feedstocks to $C_{8+}$ hydrocarbons using heterogenous catalysts. The product stream may be separated and further processed for use in chemical applications, or as a neat fuel or a blending component in jet fuel and diesel fuel, or as heavy oils for lubricant and/or fuel oil applications.

18 Claims, 9 Drawing Sheets

Related U.S. Application Data

(60) Provisional application No. 61/440,249, filed on Feb. 7, 2011.

(51) Int. Cl.
    *C10G 45/10*     (2006.01)
    *C10L 1/04*     (2006.01)
    *C10L 1/08*     (2006.01)
    *C10G 3/00*     (2006.01)

(52) U.S. Cl.
CPC ........... *C10G 2300/1014* (2013.01); *C10G 2300/202* (2013.01); *C10G 2300/301* (2013.01); *C10G 2300/4037* (2013.01); *C10G 2300/4081* (2013.01); *C10G 2300/805* (2013.01); *C10G 2400/02* (2013.01); *C10G 2400/04* (2013.01); *C10G 2400/08* (2013.01); *Y02P 20/582* (2015.11); *Y02P 30/20* (2015.11)

(56) References Cited

U.S. PATENT DOCUMENTS

| | | |
|---|---|---|
| 6,964,757 B2 | 11/2005 | Cortright et al. |
| 7,767,867 B2 | 8/2010 | Cortright |
| 7,977,517 B2 | 7/2011 | Cortright et al. |
| 8,017,818 B2 | 9/2011 | Cortright et al. |
| 8,053,615 B2 | 11/2011 | Cortright et al. |
| 2007/0135316 A1 | 6/2007 | Koivusalmi et al. |
| 2007/0249872 A1* | 10/2007 | Komplin et al. ............ 568/881 |
| 2009/0211942 A1 | 8/2009 | Cortright et al. |
| 2010/0076233 A1 | 3/2010 | Cortright et al. |
| 2011/0263916 A1* | 10/2011 | Bao ......................... C01B 3/38 585/254 |

OTHER PUBLICATIONS

Huber, et al., An Overview of Aqueous-Phase Catalytic Processes for Production of Hydrogen and Alkanes in a Biorefinery, Catalysis Today, 2006, 111:119-132.

PCT International Search Report and Written Opinion, PCT/US2012/024144, Jul. 5, 2012.

* cited by examiner

US 9,593,054 B2

PRODUCTION OF DISTILLATE FUELS FROM BIOMASS-DERIVED POLYOXYGENATES

CROSS REFERENCE TO RELATED APPLICATIONS

This application is a continuation-in-part of U.S. application Ser. No. 13/368,023 filed Feb. 7, 2012, which claimed the benefit of U.S. Provisional Application No. 61/440,249 filed Feb. 7, 2011.

STATEMENT REGARDING FEDERALLY SPONSORED RESEARCH

This invention was made with government support under Contract No. DE-EE0005006 awarded by the United States Department of Energy. The government has certain rights in the invention.

TECHNICAL FIELD

The present invention is directed to methods, catalysts and reactor systems for producing jet, diesel and heavy oil fuel from biomass and biomass-derived feedstocks using heterogeneous catalysts.

BACKGROUND OF THE INVENTION

Significant amount of attention has been placed on developing new technologies for providing energy from resources other than fossil fuels. Biomass is a resource that shows promise as a fossil fuel alternative. As opposed to fossil fuel, biomass is also renewable.

One type of biomass is plant biomass. Plant biomass is the most abundant source of carbohydrate in the world due to the lignocellulosic materials in its cell walls. Plant cell walls are divided into two sections, primary cell walls and secondary cell walls. The primary cell wall provides structure for expanding cells and is composed of major polysaccharides (cellulose, pectin, and hemicellulose) and glycoproteins. The secondary cell wall, which is produced after the cell has finished growing, also contains polysaccharides and is strengthened through polymeric lignin covalently cross-linked to hemicellulose. Cellulose includes high molecular weight polymers formed of tightly linked glucose monomers, while hemicellulose includes shorter polymers formed of various sugars. Lignin includes phenylpropanoic acid moieties polymerized in a complex three dimensional structure. Overall, the composition of the lignocellulosic biomass is roughly 40-50% cellulose, 20-25% hemicellulose, and 25-35% lignin, by weight percent.

Most transportation vehicles, whether boats, trains, planes and automobiles, require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier. This is why most fuels are liquids.

Currently, biomass provides the only renewable alternative for liquid transportation fuel. Unlike nuclear and wind applications, and for the most part solar resources, biomass is capable of being converted into a liquid form. Unfortunately, the progress in developing new technologies for producing liquid biofuels has been slow, especially for liquid fuel products appropriate for jet, diesel and heavy fuel oil applications. Although a variety of jet and diesel fuels can be produced from biomass resources, such as biodiesel, Fischer-Tropsch diesel, and jatropha and palm oil jet fuels, these fuels are often limited in their use due to their respective characteristics. The production of these fuels also tends to be expensive and raises questions with respect to net carbon savings.

Biodiesel, for example, can be made from vegetable oil, animal fats, waste vegetable oils, microalgae oils or recycled restaurant greases, and is produced through a process in which organically derived oils are combined with alcohol (ethanol or methanol) in the presence of a catalyst to form ethyl or methyl esters. The biomass-derived ethyl or methyl esters can then be blended with conventional diesel fuel or used as a neat fuel (100% biodiesel). Biodiesel is also expensive to manufacture, and poses various issues in its use and combustion. For example, biodiesel is not suitable for use in lower temperatures and requires special handling to avoid gelling in cold temperatures. Biodiesel also tends to provide higher nitrogen oxide emissions and cannot be transported in petroleum pipelines.

Biomass can also be gasified to produce a synthesis gas composed primarily of hydrogen and carbon monoxide, also called syngas or biosyngas. Syngas produced today is used directly to generate heat and power, but several types of biofuels may be derived from syngas. Hydrogen can be recovered from syngas, or the syngas can be catalytically converted to methanol. Using Fischer-Tropsch catalysts, the gas can also be converted into a liquid stream with properties similar to diesel fuel. These processes are energy and capital intensive, and are limited by the availability of biomass at volumes appropriate for the scale needed to be commercially effective.

The above technologies are also inefficient and either fail to make use of the plant's carbohydrate material or require the total destruction and reassembly of its carbon backbone. Bioreforming processes have recently been developed to overcome these issues and provide liquid fuels and chemicals derived from the cellulose, hemicellulose and lignin found in plant cell walls. For instance, cellulose and hemicellulose can be used as feedstock for various bioreforming processes, including aqueous phase reforming (APR) and hydrodeoxygenation (HDO)—catalytic reforming processes that, when integrated with hydrogenation, can convert cellulose and hemicellulose into hydrogen and hydrocarbons, including liquid fuels and other chemical products. APR and HDO methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867; 7,989,664; and 8,198,486; and U.S. Application No. 2012/0283478 (all to Cortright, and entitled "Methods and Systems for Generating Polyols"). Various APR and HDO methods and techniques are described in U.S. Pat. Nos. 8,053,615; 8,017,818; 7,977,517; 8,362,307; 8,367,882; and U.S. Patent Application Ser. Nos. 2011/0245542 and 2011/0257448 (all to Cortright and Blommel, and entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Pat. No. 8,350,108 (to Cortright et al., and entitled "Synthesis of Liquid Fuels from Biomass"); U.S. patent application Ser. No. 13/586,499 (to Blank et al. and entitled "Improved Catalysts for the Hydrodeoxygenation of Oxygenated Hydrocarbons"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference. Additional techniques for converting cellulose, hemicellulose and lignin to useable feedstocks for the above APR and HDO processes are described in U.S. Patent Application Ser. No. 2012/0167875 (to Qiao et al., and entitled "Solvolysis of Biomass Using Solvent from a Bioforming Process"); U.S. Patent Application Ser. No. 2012/0167876 (to Qiao et al., and entitled "Organo-Catalytic Biomass Deconstruction"); U.S. Patent Application Ser. No. 2012/0172588 (to Qiao et al., and entitled "Catalytic Biomass Deconstruction"); U.S. Patent Application Ser. No. 2012/0172579 (to Qiao et al., and entitled "Reductive Biomass Liquefaction"); U.S. Patent Application Ser. No. 2013/0036660 (to Woods et al. and entitled "Production of Chemicals and Fuels from Biomass"); U.S. Patent Application Ser. No. 2012/0280175 (to Kania et al. and entitled "Apparatus and Method for Converting Biomass to Feedstock for Biofuel and Biochemical Manufacturing Processes"); U.S. Patent Application Ser. No. 2012/0289692 (to Gray et al. and entitled "Process for Purifying Lignocellulosic Feedstocks"); U.S. Patent Application Ser. No. 2012/0323053 (to Qiao et al. and entitled "Methods for Biomass Deconstruction and Purification"); U.S. Patent Application Ser. No. 2013/0023702 (to Qiao et al. and entitled "Serial Deconstruction of Biomass"); U.S. Patent Application Ser. No. 2013/0019859 (to Qiao et al. and entitled "Solvolysis of Biomass and Stabilization of Biomass Hydrolysate"); and U.S. Patent Application Ser. No. 2012/0318258 (to Qiao et al. and entitled "Solvolysis of Biomass to Produce Aqueous and Organic Products").

One of the keys to commercializing the above technologies is to further refine the processes to maximize product yield and extend catalyst lifetime. Also of interest is the ability to tailor the reactions to produce specific products of high demand or of higher commercial value. Accordingly, what is needed is a more refined process for converting biomass and biomass-derived feedstocks to a greater quantity of heavier hydrocarbons useful in jet and diesel fuels, or as heavy oils for lubricant and/or fuel oil applications.

SUMMARY

The invention provides methods for making $C_{8+}$ compounds. The method generally involves providing a reactant stream comprising a first reactant and a second reactant and catalytically reacting the reactant stream with hydrogen in the presence of an acid condensation catalyst to produce a product stream comprising water and a plurality of $C_{8+}$ compounds. The first reactant comprises one or more molecules having a general formula $C_xH_yO_z$ and a first reactant average oxygen to carbon ratio of between 0.2 and 1.0, and x=2-12 carbon atoms and z=1-12 oxygen atoms. The second reactant comprises one or more molecules having a general formula $C_pH_rO_s$ and a second reactant average oxygen to carbon ratio of 0.2 or less, and p=2-7 carbon atoms and s=0-1 oxygen atoms. The number of carbon atoms in the reactant stream from the first reactant is greater than 10% of the total carbon atoms in the reactant stream, and the number of carbon atoms in the reactant stream from the second reactant is greater than 10% of the total carbon atoms in the reactant stream. The product stream comprises water and a plurality of $C_{8+}$ compounds selected from the group consisting of $C_{8+}$ alkanes, $C_{8+}$ alkenes, $C_{8+}$ cycloalkanes, $C_{8+}$ cycloalkenes, $C_{8+}$ alcohols, $C_{8+}$ ketones, an aryl, a fused aryl, an oxygenated aryl, an oxygenated fused aryl, and a mixture thereof. The acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof.

One aspect of the invention is the catalytic material. In one embodiment, the acidic support is selected from the group consisting of an aluminosilicate, a tungstated aluminosilicate, a silica-alumina phosphate, an aluminum phosphate, an amorphous silica alumina, an acidic alumina, a phosphate alumina, a tungstated alumina, a zirconia, a tungstated zirconia, a tungstated silica, a tungstated titania, a tungstated phosphate, niobia, an acid modified resin, a zeolite, a heteropolyacid, a tungstated heteropolyacid, and combinations thereof. The heterogeneous acidic catalyst may further comprise a support selected from the group consisting of carbon, silica, alumina, zirconia, titania, vanadia, kieselguhr, hydroxyapatite, chromia, niobia, mixtures thereof, and combinations thereof. In another embodiment, the acid condensation catalyst further comprises a modifier selected from the group consisting of Cu, Ag, Au, Ru, Pd, Ni, Co, Ga, In, Cr, Mo, W, Sn, Nb, Ti, Zr, Ge, P, Al, alloys thereof, and combinations thereof. In certain embodiments, the acid condensation catalyst comprises ZSM-5 or tungstated zirconia. The acid condensation catalyst may further comprise Pd or Cu.

Another aspect of the invention is the composition of the reactant streams. In one embodiment, the second reactant has an average oxygen to molecule ratio of 1 to 4, and the first reactant has an average oxygen to molecule ratio of 1.5 or less. In another embodiment, the second reactant has a boiling point of less than 210° C. In yet another embodiment, the reactant stream further includes water.

The product stream further comprises one or more $C_{7-}$ compounds having 2 to 7 carbon atoms and 0 to 1 oxygen atoms, and a portion of the product stream may be recycled to form part of the second reactant.

The method may further comprise the following steps: (1) removing water from the product stream prior to recycling the portion of the product stream to form in part the second reactant; (2) catalytically reacting at least a portion of the product stream in the presence of a finishing catalyst; or (3) providing hydrogen, water and a water soluble oxygenated hydrocarbon comprising a $C_{2+}O_{1+}$ hydrocarbon, and catalytically reacting the oxygenated hydrocarbon with the hydrogen in the presence of a deoxygenation catalyst to produce the first reactant.

The deoxygenation catalyst is capable of converting the first reactant stream to oxygenates. In one embodiment, the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, an alloy thereof, and a combination thereof. The support may be selected from the group consisting of a carbon, silica, alumina, zirconia, titania, vanadia, heteropolyacid, kieselguhr, hydroxyapatite, chromia, zeolite, and mixtures thereof. In one embodiment, the support is selected from the group consisting of tungstated zirconia, tungsten modified zirconia, tungsten modified alpha-alumina, or tungsten modified theta alumina.

The water soluble oxygenated hydrocarbon may be selected from the group consisting of a starch, a carbohydrate, a polysaccharide, a disaccharide, a monosaccharide, a sugar, a sugar alcohol, an aldopentose, an aldohexose, a ketotetrose, a ketopentose, a ketohexose, a hemicellulose, a cellulosic derivative, a lignocellulosic derivative, and a polyol.

The hydrogen may be in situ-generated $H_2$, external $H_2$, or recycled $H_2$. In one embodiment, the hydrogen may be generated in situ by catalytically reacting in a liquid phase or vapor phase an aqueous feedstock solution comprising water and an oxygenated hydrocarbon in the presence of an aqueous phase reforming catalyst at a reforming temperature and reforming pressure.

Another aspect of the invention is a method of making $C_{8+}$ compounds by: (i) providing a reactant stream comprising water, a first reactant and a second reactant; and (ii) catalytically reacting the reactant stream with hydrogen in the presence of an acid condensation catalyst to produce a product stream comprising water and a plurality of $C_{8+}$ compounds. The first reactant may comprise one or more molecules having a general formula $C_xH_yO_z$ and a first reactant average oxygen to carbon ratio of between 0.2 and 1.0, and x=2-12 carbon atoms and z=1-12 oxygen atoms. The second reactant may comprise one or more molecules having a general formula $C_pH_rO_s$ and a second reactant average oxygen to carbon ratio of 0.2 or less, and p=2-7 carbon atoms and s=0-1 oxygen atoms. The number of carbon atoms in the reactant stream from the first reactant is greater than 10% of the total carbon atoms in the reactant stream, and the number of carbon atoms in the reactant stream from the second reactant is greater than 10% of the total carbon atoms in the reactant stream. The $C_{8+}$ compounds are selected from the group consisting of a $C_{8+}$ alkane, a $C_{8+}$ alkene, a $C_{8+}$ cycloalkane, a $C_{8+}$ cycloalkene, a $C_{8+}$ alcohol, a $C_{8+}$ ketone, an aryl, a fused aryl, an oxygenated aryl, an oxygenated fused aryl, and a mixture thereof. The acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof.

In one embodiment, the method further includes providing hydrogen, water and a water soluble oxygenated hydrocarbon comprising a $C_{2+}O_{1+}$ hydrocarbon, and catalytically reacting the oxygenated hydrocarbon with the hydrogen in the presence of a deoxygenation catalyst to produce the first reactant.

The deoxygenation catalyst is capable of converting the oxygenated hydrocarbons to oxygenates. In one embodiment, the deoxygenation catalyst comprises a support and a member selected from the group consisting of Re, Cu, Fe, Ru, Ir, Co, Rh, Pt, Pd, Ni, W, Os, Mo, Ag, Au, an alloy thereof, an alloy thereof, and a combination thereof. The support may be selected from the group consisting of a carbon, silica, alumina, zirconia, titania, vanadia, heteropolyacid, kieselguhr, hydroxyapatite, chromia, zeolite, and mixtures thereof. In one embodiment, the support is selected from the group consisting of tungstated zirconia, tungsten modified zirconia, alpha alumina, theta alumina, tungsten modified alpha-alumina, or tungsten modified theta alumina.

The water soluble oxygenated hydrocarbon may be selected from the group consisting of a starch, a carbohydrate, a polysaccharide, a disaccharide, a monosaccharide, a sugar, a sugar alcohol, an aldopentose, an aldohexose, a ketotetrose, a ketopentose, a ketohexose, a hemicellulose, a cellulosic derivative, a lignocellulosic derivative, and a polyol.

Another aspect of the present invention is a method of making $C_{8+}$ compounds comprising: (i) providing a reactant stream comprising a first reactant and a second reactant; (ii) catalytically reacting the reactant stream with hydrogen in the presence of an acid condensation catalyst to produce a product stream comprising water, a plurality of $C_{7-}$ compounds and a plurality of $C_{8+}$ compounds; (iii) separating a portion of the $C_{7-}$ compounds from the product stream to provide a recycle stream, and (iv) recycling the recycle stream to form at least in part the second reactant.

The first reactant may comprise one or more molecules having a general formula $C_xH_yO_z$ and a first reactant average oxygen to carbon ratio of between 0.2 and 1.0, and x=2-12 carbon atoms and z=1-12 oxygen atoms. The second reactant may comprise one or more molecules having a general formula $C_pH_rO_s$ and a second reactant average oxygen to carbon ratio of 0.2 or less, and p=2-7 carbon atoms and s=0-1 oxygen atoms. The number of carbon atoms in the reactant stream from the first reactant is greater than 10% of the total carbon atoms in the reactant stream, and the number of carbon atoms in the reactant stream from the second reactant is greater than 10% of the total carbon atoms in the reactant stream. The $C_{7-}$ compounds are selected from the group consisting of a $C_{7-}$ alkane, a $C_{7-}$ alkene, a $C_{7-}$ cycloalkane, a $C_{7-}$ cycloalkene, a $C_{7-}$ alcohol, a $C_{7-}$ ketone, a $C_{7-}$ aryl, and mixtures thereof. The $C_{8+}$ compounds are selected from the group consisting of a $C_{8+}$ alkane, a $C_{8+}$ alkene, a $C_{8+}$ cycloalkane, a $C_{8+}$ cycloalkene, a $C_{8+}$ alcohol, a $C_{8+}$ ketone, an aryl, a fused aryl, an oxygenated aryl, an oxygenated fused aryl, and a mixture thereof. The acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof.

In one embodiment, the acidic support is selected from the group consisting of an aluminosilicate, a tungstated aluminosilicate, a silica-alumina phosphate, an aluminum phosphate, an amorphous silica alumina, an acidic alumina, a phosphate alumina, a tungstated alumina, a zirconia, a tungstated zirconia, a tungstated silica, a tungstated titania, a tungstated phosphate, niobia, an acid modified resin, a zeolite, a heteropolyacid, a tungstated heteropolyacid, and combinations thereof. The heterogeneous acidic catalyst may further comprise a support selected from the group consisting of carbon, silica, alumina, zirconia, titania, vanadia, kieselguhr, hydroxyapatite, chromia, niobia, mixtures thereof, and combinations thereof. The acid condensation catalyst further comprises a modifier selected from the group consisting of Cu, Ag, Au, Ru, Pd, Ni, Co, Ga, In, Cr, Mo, W, Sn, Nb, Ti, Zr, Ge, P, Al, alloys thereof, and combinations thereof.

In one embodiment, the acid condensation catalyst comprises ZSM-5 or tungstated zirconia. The acid condensation catalyst may further comprises Pd or Cu.

In another embodiment, the second reactant has an average oxygen to molecule ratio of 1 to 4, and the first reactant has an average oxygen to molecule ratio of 1.5 or less. In yet another embodiment, the recycle stream has a boiling point of less than 210° C.

Another aspect of the invention is a method of making a fuel product comprising: (i) providing a reactant stream comprising a first reactant and a second reactant; (ii) catalytically reacting the reactant stream with hydrogen in the presence of an acid condensation catalyst to produce a product stream comprising water, a plurality of $C_{7-}$ compounds and a plurality of $C_{8+}$ compounds; (iii) separating at least a portion of the $C_{8+}$ compounds from the product stream, (iv) catalytically reacting the separated $C_{8+}$ compounds in the presence of a finishing catalyst to produce a fuel product.

The first reactant may comprise one or more molecules having a general formula $C_xH_yO_z$ and a first reactant average oxygen to carbon ratio of between 0.2 and 1.0, and x=2-12 carbon atoms and z=1-12 oxygen atoms. The second reactant may comprise one or more molecules having a general formula $C_pH_rO_s$ and a second reactant average oxygen to carbon ratio of 0.2 or less, and p=2-7 carbon atoms and s=0-1 oxygen atoms. The number of carbon atoms in the reactant stream from the first reactant is greater than 10% of the total carbon atoms in the reactant stream, and the number of carbon atoms in the reactant stream from the second reactant is greater than 10% of the total carbon atoms in the reactant stream. The $C_{7-}$ compounds are selected from the group consisting of a $C_{7-}$ alkane, a $C_{7-}$ alkene, a $C_{7-}$ cycloalkane, a $C_{7-}$ cycloalkene, a $C_{7-}$ alcohol, a $C_{7-}$ ketone, a $C_{7-}$ aryl, and mixtures thereof. The $C_{8+}$ compounds are selected from the group consisting of a $C_{8+}$ alkane, a $C_{8+}$ alkene, a $C_{8+}$ cycloalkane, a $C_{8+}$ cycloalkene, a $C_{8+}$ alcohol, a $C_{8+}$ ketone, an aryl, a fused aryl, an oxygenated aryl, an oxygenated fused aryl, and a mixture thereof. The acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof.

In one embodiment, the method further comprises a step of separating the fuel product to provide a $C_{8-14}$ fraction comprising a plurality of hydrocarbons having 8 to 14 carbon atoms, a $C_{12-24}$ fraction comprising a plurality of hydrocarbons having 12 to 24 carbon atoms, and a $C_{25+}$ fraction comprising a plurality of hydrocarbons having 25 or more carbon atoms. In another embodiment, the $C_{8-14}$ fraction is blended to provide a jet fuel, or the $C_{12-24}$ fraction is blended to provide a diesel fuel, or the $C_{25+}$ fraction is blended to provide a heavy oil.

The invention provides additional methods for making $C_{8+}$ compounds. These methods generally involve providing a reactant stream comprising a first reactant and a second reactant and catalytically reacting the reactant stream with hydrogen in the presence of an acid condensation catalyst to produce a product stream comprising water and a plurality of $C_{8+}$ compounds. The first reactant comprises one or more molecules having a general formula $C_xH_yO_z$ and a first reactant average oxygen to carbon ratio of between 0.08 and 0.75, and x=2-12 carbon atoms and z=1-3 oxygen atoms. The second reactant comprises one or more molecules having a general formula $C_pH_rO_s$ and a second reactant average oxygen to carbon ratio of less than 0.2, and p=2-7 carbon atoms and s=0-1 oxygen atoms. The number of carbon atoms in the reactant stream from the first reactant is greater than 10% of the total carbon atoms in the reactant stream, and the number of carbon atoms in the reactant stream from the second reactant is greater than 10% of the total carbon atoms in the reactant stream. The first reactant comprises at least one member selected from the group consisting of a ketone, an alcohol, an aldehyde, a carboxylic acid, a cyclic ether, a hydroxyketone, a lactone, a diol, a triol, and mixtures thereof. The product stream comprises water and a plurality of $C_{8+}$ compounds selected from the group consisting of $C_{8+}$ alkanes, $C_{8+}$ alkenes, $C_{8+}$ cycloalkanes, $C_{8+}$ cycloalkenes, $C_{8+}$ alcohols, $C_{8+}$ ketones, an aryl, a fused aryl, an oxygenated aryl, an oxygenated fused aryl, and a mixture thereof. The acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof.

In one embodiment, the second reactant further comprises one or more molecules having a general formula $C_jH_kO_m$ and a third reactant average oxygen to carbon ratio of between 0.14 and 0.67 and wherein j=3-7 carbon atoms and m=1-2 oxygen atoms.

In one embodiment, the second reactant comprises at least one member selected from the group consisting of a ketone, an alcohol, an aldehyde, a diol, a ketone, an alcohol, an aldehyde, a carboxylic acid, a cyclic ether, a diol, a hydroxyketone, a lactone, and mixtures thereof.

Another aspect of the invention is the catalytic material. In one embodiment, the acidic support is selected from the group consisting of an aluminosilicate, a tungstated aluminosilicate, a silica-alumina phosphate, an aluminum phosphate, an amorphous silica alumina, an acidic alumina, a phosphate alumina, a tungstated alumina, a zirconia, a tungstated zirconia, a tungstated silica, a tungstated titania, a tungstated phosphate, niobia, an acid modified resin, a zeolite, a heteropolyacid, a tungstated heteropolyacid, and combinations thereof. The heterogeneous acidic catalyst may further comprise a support selected from the group consisting of carbon, silica, alumina, zirconia, titania, vanadia, kieselguhr, hydroxyapatite, chromia, niobia, mixtures thereof, and combinations thereof. In another embodiment, the acid condensation catalyst further comprises a modifier selected from the group consisting of Cu, Ag, Au, Ru, Pd, Ni, Co, Ga, In, Cr, Mo, W, Sn, Nb, Ti, Zr, Ge, P, Al, alloys thereof, and combinations thereof. In certain embodiments, the acid condensation catalyst comprises ZSM-5 or tungstated zirconia. The acid condensation catalyst may further comprise Pd, Cu, Ag, and combinations thereof.

In another embodiment, the product stream may comprise one or more $C_{7-}$ compounds having 3 to 7 carbon atoms and 0 to 2 oxygen atoms, and a portion of the product stream may be recycled to form at least a part of the second reactant stream.

The method may further comprise the following steps: (1) removing water from the product stream prior to recycling the portion of the product stream to form in part the second reactant; (2) catalytically reacting at least a portion of the product stream in the presence of a finishing catalyst; or (3) providing hydrogen, water and a water soluble oxygenated hydrocarbon comprising a $C_{2+}O_{1+}$ hydrocarbon, and catalytically reacting the oxygenated hydrocarbon with the hydrogen in the presence of a deoxygenation catalyst to produce the first reactant.

The deoxygenation catalyst is capable of converting the oxygenated hydrocarbons to oxygenates. In one embodiment, the deoxygenation catalyst comprises a support and a member selected from the group consisting of Re, Cu, Fe, Ru, Ir, Co, Rh, Pt, Pd, Ni, W, Os, Mo, Ag, Au, Sn, an alloy thereof, an alloy thereof, and a combination thereof. The support may be selected from the group consisting of a carbon, silica, alumina, zirconia, titania, vanadia, heteropolyacid, kieselguhr, hydroxyapatite, chromia, zeolite, and mixtures thereof. In one embodiment, the support is selected from the group consisting of tungstated zirconia, tungsten modified zirconia, alpha alumina, tungsten modified alpha-alumina, theta alumina, or tungsten modified theta alumina.

The water soluble oxygenated hydrocarbon may be selected from the group consisting of a starch, a carbohydrate, a polysaccharide, a disaccharide, a monosaccharide, a sugar, a sugar alcohol, an aldopentose, an aldohexose, a ketotetrose, a ketopentose, a ketohexose, a hemicellulose, a cellulosic derivative, a lignocellulosic derivative, and a polyol.

The hydrogen may be in situ-generated $H_2$, external $H_2$, or recycled $H_2$. In one embodiment, the hydrogen may be generated in situ by catalytically reacting in a liquid phase or vapor phase an aqueous feedstock solution comprising water and an oxygenated hydrocarbon in the presence of an aqueous phase reforming catalyst at a reforming temperature and reforming pressure.

DETAILED DESCRIPTION OF THE INVENTION

Figure 1:
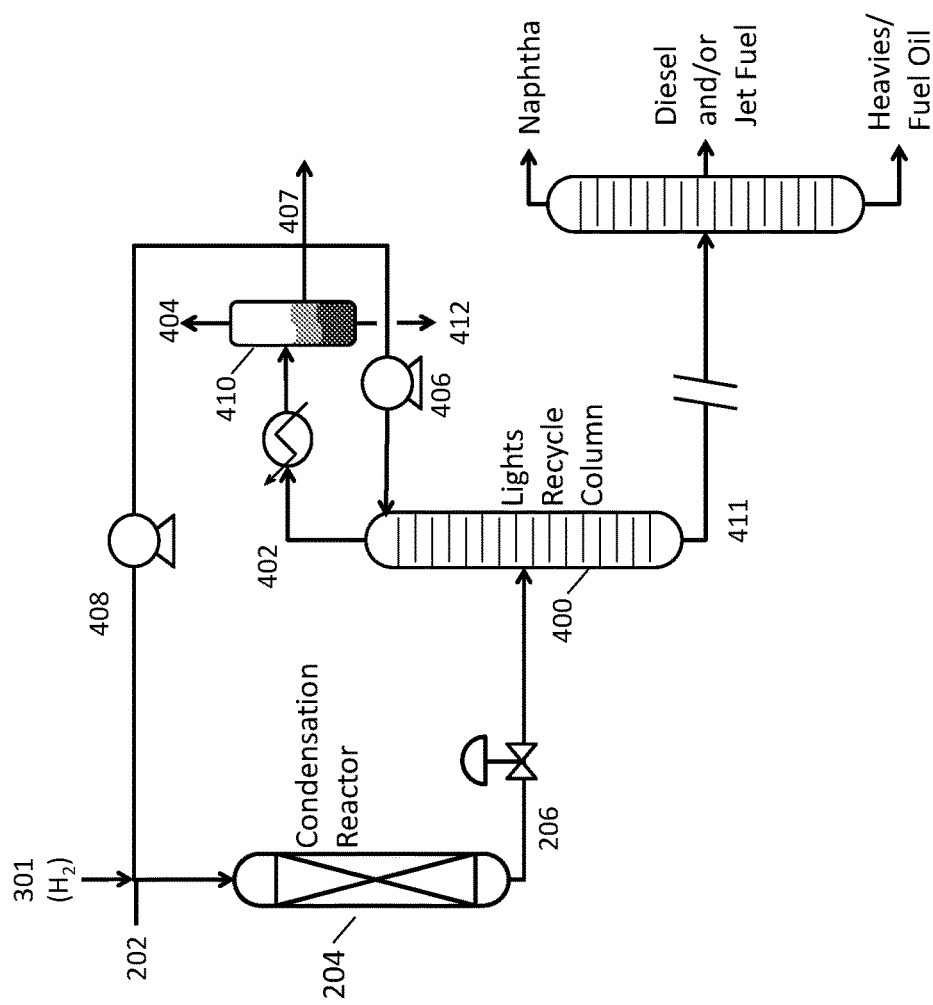
FIG. 1 is a flow diagram illustrating a reactor system for catalytically converting biomass to $C_{8+}$ compounds according to the present invention.

The present invention provides methods, reactor systems and catalysts for converting biomass and biomass-derived feedstocks to $C_{8+}$ hydrocarbons using heterogenous catalysts. The resulting product stream includes $C_{8+}$ alkanes, $C_{8+}$ alkenes, $C_{8+}$ cycloalkanes, $C_{8+}$ cycloalkenes, aryls, fused aryls, and mixtures thereof. The product stream may also include $C_{8+}$ alcohols, $C_{8+}$ ketones, oxygenated aryls, and oxygenated fused aryls. The product stream may be separated and further processed for use in chemical applications or as a neat fuel or a blending component in jet and diesel fuels or as heavy oils for lubricant and/or fuel oil applications. The overall conversion process may occur separately in different reactors or together in a single reactor, and generally occurs in a steady-state as part of a continuous process.

The invention generally involves catalytically reacting a reactant stream containing a first reactant and a second reactant with hydrogen in the presence of an acidic condensation catalyst at a condensation temperature and condensation pressure appropriate to produce a product stream containing water and $C_{8+}$ compounds. In one embodiment, the reactant stream also includes water. In another embodiment, a portion of the product stream is recycled to the feed stream to provide the second reactant. In yet another embodiment, the product stream is further processed in a finishing step to produce a fuel product appropriate for use as a neat fuel or as a blending component for jet, diesel or heavy oil applications. In still yet another embodiment, the fuel product is blended with other hydrocarbons to provide a final jet fuel, diesel fuel or heavy oil product.

The reactant stream may originate from any source, but is preferably derived from biomass or a biomass-derived feedstock using any known method. Such methods include fermentation technologies using enzymes or microorganisms, Fischer-Tropsch reactions to produce $C_{2-10}$ alpha alcohols and other oxygenates, and pyrolysis technologies to produce alcohols from oil, among others. In one embodiment, the reactant stream is produced using a catalytic bioreforming technology, such as an APR and/or HDO catalytic process.

The hydrogen may be generated in situ using aqueous phase reforming (in situ-generated $H_2$ or APR $H_2$), or a combination of APR $H_2$, external $H_2$ and/or recycled $H_2$, or just simply external $H_2$ or recycled $H_2$. The term "external $H_2$" refers to hydrogen that does not originate from the feedstock, but is added to the reactor system from an external source. The term "recycled $H_2$" refers to unconsumed hydrogen, which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen, to increase the reaction pressure within the system, or to increase the molar ratio of hydrogen to carbon and/or oxygen in order to enhance the production yield of certain reaction product types.

A surprising aspect of the invention is that the inventors are able to increase the production yield of $C_{8+}$ compounds by using the below described acid condensation catalysts and a reactant stream that includes a first reactant having an average oxygen to carbon ratio of between 0.2 and 1.0, or between 0.08 and 0.75, and a second reactant having an average oxygen to carbon ratio of 0.2 or less, or between 0.14 and 0.67, in the presence of water. Without being bound to any particular theory, it is believed that the unique combination of the first and second reactants in the reactant stream helps control the effects of water in the system and drives the reaction to produce the longer chain $C_{8+}$ compounds. Specifically, it is believed that the combination of the reactants has the effect of increasing the reaction partial pressure for the reactants, while decreasing the partial pressure of water. The resulting product stream tends to have a greater yield of $C_{8+}$ compounds as compared to systems not involving a second reactant as described herein.

The first reactant includes one or more oxygenates having a general formula $C_xH_yO_z$, with x representing 2 to 12 carbon atoms and z representing 1 to 12 oxygen atoms. Alternatively, the first reactant may have between 2 to 12 carbon atoms and between 1 to 3 oxygen atoms. Collectively, the average oxygen to carbon ratio of the oxygenates in the first reactant should be about 0.2 to 1.0, or 0.08 to 0.75, calculated as the total number of oxygen atoms (z) in the oxygenates of the first reactant divided by the total number of carbon atoms (x) in the oxygenates of the first reactant. Alternatively, the first reactant may have an average oxygen content per molecule of about 1 to 4, calculated as the total number of oxygen atoms (z) in the oxygenates of the first reactant divided by the total number of molecules of oxygenates in the first reactant. The total number of carbon atoms per molecule, oxygen atoms per molecule and total molecules in the first reactant may be measured using any number of commonly known methods, including (1) speciation by gas chromatography (GC), high performance liquid chromatrography (HPLC), and other methods known to the art and (2) determination of total oxygen, carbon, and water content by elemental analysis. Oxygen present in water, carbon dioxide, or carbon monoxide is excluded from the determination of reactant oxygen to carbon ratio.

Examples of oxygenates in the first reactant include, without limitation, oxygenated hydrocarbons having 1 to 4 oxygen atoms (e.g., mono-, di-, tri- and tetra-oxygenated hydrocarbons), or oxygenated hydrocarbons having 1 to 3 oxygen atoms (e.g., mono-, di-, and tri oxygenated hydrocarbons). The mono-oxygenated hydrocarbons typically include alcohols, ketones, aldehydes, cyclic ethers, furans, and pyrans, while the di-oxygenated hydrocarbons typically include diols, hydroxy ketones, lactones, furfuryl alcohols, pyranyl alcohols, and carboxylic acids. Alcohols may include, without limitation, primary, secondary, linear, branched or cyclic $C_{2+}$ alcohols, such as ethanol, n-propyl alcohol, isopropyl alcohol, 1-butanol, 2-butanol, 2-methyl-1-propanol (isobutyl alcohol), 2-methyl-2-propanol (tert butyl alcohol), 1-pentanol, 2-pentanol, 3-pentanol, cyclopentanol, 1-hexanol, 2-hexanol, 3-hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, 2-pentanone, 3-pentanone, cyclopentanone, pentane-2,3-dione, pentane-2,4-dione, 2-hexanone, 3-hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, 2-hydroxy-propionaldehyde, butyraldehyde, 2-hydroxypropionaldehyde, 3-hydroxypropionaldehyde, 2-methyl-propanal, pentanal, hexanal, heptanal, octanal, nonal, decanal, undecanal, dodecanal, and isomers thereof. The carboxylic acids may include, without limitation, formic acid, acetic acid, propionic acid, butanoic acid, isobutyric acid, pentanoic acid, hexanoic acid, heptanoic acid, isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane (trimethylolethane), trimethylolpropane, hexanetriol, and isomers thereof. Cyclic ethers include, without limitation, tetrahydrofuran, 2-methyl-tetrahydrofuran, 2,5-dimethyl-tetrahydrofuran, 2-ethyl-tetrahydrofuran, 3-hydroxytetrahydrofuran, tetrahydro-3-furanol, tetrahydro-2-furoic acid, dihydro-5-(hydroxymethyl)-2(3H)-furanone, 1-(2-furyl)ethanol, tetrahydropyran, 2-methyltetrahydropyran, and isomers thereof. Furans include, without limitation, furfural, furan, dihydrofuran, 2-furan methanol, 2-methyl furan2-ethyl furan, hydroxylmethylfurfural, 2,5-dimethyl furan, 5-hydroxymethyl-2(5H)-furanone, dihydro-5-(hydroxymethyl)-2(3H)-furanone, tetrahydrofurfuryl alcohol, hydroxymethyltetrahydrofurfural, The second reactant includes one or more hydrocarbons and/or oxygenated hydrocarbons having a general formula $C_pH_rO_s$, with p representing 2 to 7 carbon atoms and s representing 0 to 1 oxygen atoms. Alternatively, the second reactant may have between 2 to 7 carbon atoms and 1 to 2 oxygen atoms. When the second reactant is derived from a recycle stream as described below, the second reactant may also contain residual oxygenated hydrocarbons containing 1-2 oxygen atoms. Collectively, the average oxygen to carbon ratio of the second reactant should be less than 0.2, or between 0.14 to 0.67, calculated as the total number of oxygen atoms (s) in the oxygenated hydrocarbons of the second reactant divided by the total number of carbon atoms (p) in the hydrocarbons and oxygenated hydrocarbons of the second reactant. Alternatively, the second reactant may have an average oxygen per molecule ratio of less than 1.5, calculated as the total number of oxygen atoms (s) in the oxygenated hydrocarbons of the second reactant divided by the total number of molecules of hydrocarbons and oxygenated hydrocarbons in the second reactant. The second reactant may also be characterized as having an average normal boiling point of less than 210° C., or less than 200° C., or less than 190° C.

The second reactant will generally include alkanes, alkenes, mono-oxygenated and di-oxygenated hydrocarbons (such as diols, alcohols, ketones, aldehydes, cyclic ethers), as well as residual oxygenated compounds capable of being volatilized based on the temperature, total pressure and concentration of the compounds (such as various diols and carboxylic acids). Examples of second reactant compounds include, without limitation, the $C_{7-}$ compounds listed below.

The second reactant may be provide from any source, but is preferably derived from biomass or a biomass-derived feedstock. For example, although a biomass-derived feedstock is preferred, it is contemplated that all or a portion of the second reactant may originate from fossil fuel based compounds, such as natural gas or petroleum. All or a portion of the second reactant may also originate from any one or more fermentation technologies, gasification technologies, Fischer-Tropsch reactions, or pyrolysis technologies, among others. Preferably, at least a portion of the second reactant is derived from the product stream and recycled to be combined with the first reactant to provide at least a portion of the reactant stream.

When a portion of the second reactant is derived from the product stream, the product stream is separated into a first portion containing the desired $C_{8+}$ compounds and a second portion containing the compounds to be recycled and used as a portion of the second reactant. Alternatively, the product stream may be first separated to a water fraction and an organic fraction, with the organic fraction then separated into a first portion containing the desired $C_{8+}$ compounds and a second portion containing the compounds to be recycled and used as a portion of the second reactant. Processes for separating liquid mixtures into their component parts or fractions are commonly known in the art, and often involve the use of a separator unit, such as one or more distillation columns, phase separators, extractors, purifiers, among others.

In one embodiment, the separation step includes one or more distillation columns designed to facilitate the separation of the $C_{8+}$ compounds from the product stream or, alternatively, the separation from the product stream of the second portion containing the compounds to be recycled and used as a portion of the second reactant. The distillation will be generally operated at a temperature, pressure, reflux ratio, and with an appropriate equipment design, to recover the second portion as an overhead product which conforms to the boiling point characteristics described above. The first portion, containing the $C_{8+}$ compounds, and with a higher average boiling point profile than the second portion, will be taken as a high boiling bottoms product which may be further processed to effect further separations.

The composition of the reactant stream will depend on the concentration of the water (if any), the first reactant and the second reactant in the reactant stream. In one embodiment, the mass flow rate of the second reactant is set such that the mass ratio of the second reactant to the first reactant is greater than 5%, or greater than 10%, or greater than 20%, or greater than 30%. Alternatively, the first reactant and second reactant may be combined such that the mass fraction of oxygen in the combined reactant stream is at least 10% lower, or 20% lower, or 30% lower, or 40% lower than the mass fraction of oxygen in the first reactant alone.

Figure 8:
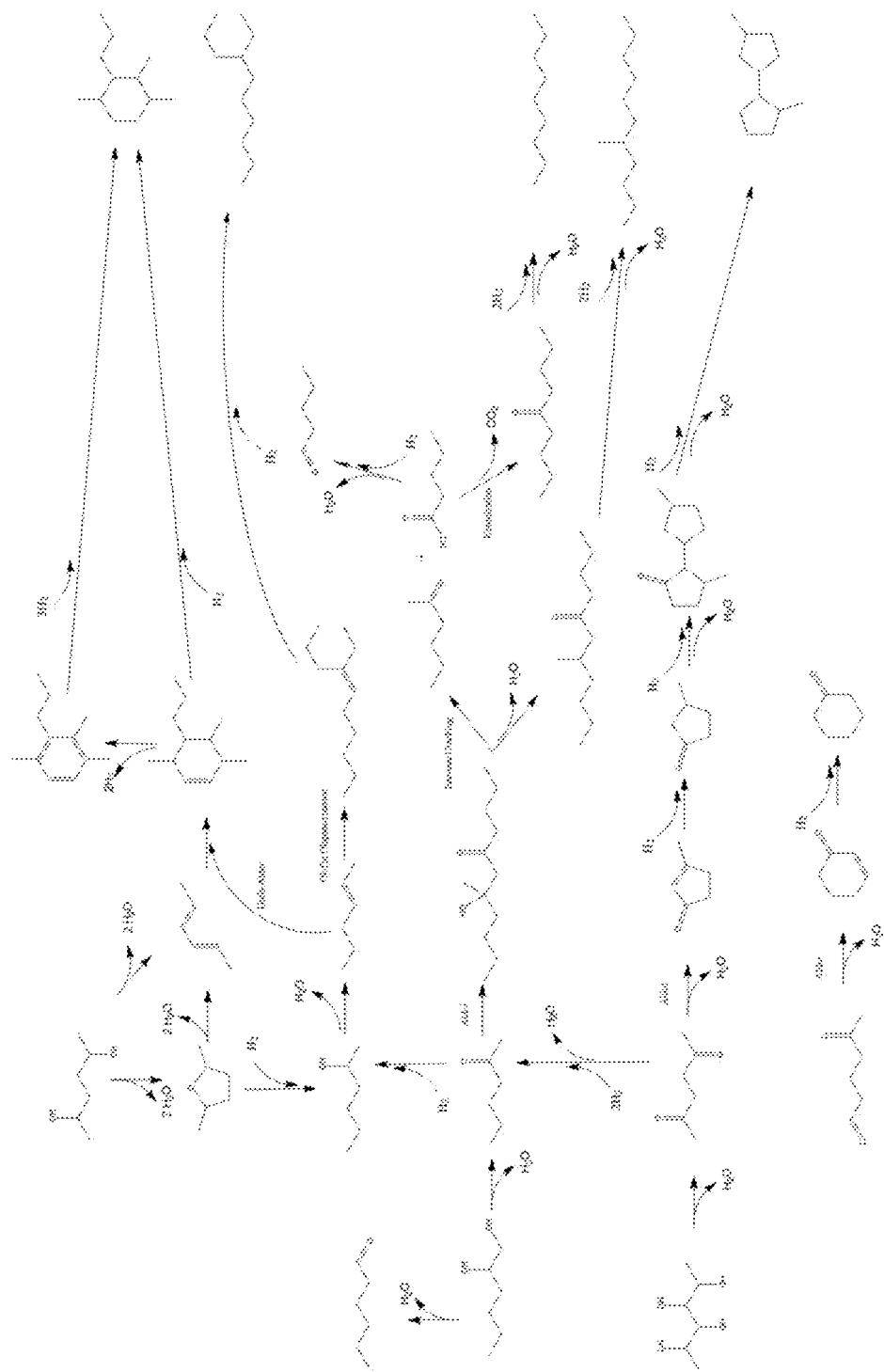
FIG. 8 is an illustration of various chemical pathways believed to be involved in the production of $C_{8+}$ compounds according to the present invention.

The condensation reaction is performed using catalytic materials that exhibit acidic activity. These materials may be augmented through the addition of a metal to allow activation of molecular hydrogen for hydrogenation/dehydrogenation reactions. Without being limited to any specific theories, it is believed that the reactions generally consist of a series of steps schematically shown in FIG. 8. The steps involve removal of oxygen, formation of carbon-carbon bonds to form larger carbon containing species, cyclization reactions, and hydrogenation reactions. Oxygen removal steps include: (a) dehydration of alcohols to form alkenes; (b) hydrogenolysis of alcohols; (c) hydrogenation of carbonyls to alcohols followed by dehydration; and (d) ketonization of organic acids. Within the condensation system, the oxygen removal steps allow the processing of compounds containing 1, 2, 3, 4, 5 or 6 oxygen atoms. Carbon-carbon bond formation to create larger carbon containing species takes place via: (a) oligomerization of alkenes; (b) aldol condensation to form α-hydroxyketones α-hydroxyaldehydes; (c) hydrogenation of the conjugated enones to form ketones or aldehydes, which may participate in further condensation reactions or convert to alcohols or hydrocarbons; (d) Prins reactions between alkenes and aldehydes; and (e) ketonization of organic acids. Acid catalyzed pathways to form cyclic compounds include: (a) intra-molecular aldol condensations; and (b) dehydration of cyclic ethers to form dienes with subsequent reaction of the diene with an alkene via a Diel-Alder condensation. Finally, alkenes may be hydrogenated either via hydride transfer and/or via a hydrogenation pathway utilizing metals added to the acidic materials.

The acid condensation catalyst may be either an acidic support or an acidic heterogeneous catalyst comprising a support and an active metal, such as Pd, Pt, Cu, Co, Ru, Cr, Ni, Ag, alloys thereof, or combinations thereof. The acid condensation catalyst may include, without limitation, aluminosilicates, tungstated aluminosilicates, silica-alumina phosphates (SAPOs), aluminum phosphates (ALPO), amorphous silica alumina (ASA), acidic alumina, phosphated alumina, tungstated alumina, zirconia, tungstated zirconia, tungstated silica, tungstated titania, tungstated phosphates, acid modified resins, heteropolyacids, tungstated heteropolyacids, silica, alumina, zirconia, titania, tungsten, niobia, zeolites, mixtures thereof, and combinations thereof. The acid condensation catalyst may include the above alone or in combination with a modifier or metal, such as Re, Cu, Fe, Ru, Ir, Co, Rh, Pt, Pd, Ni, W, Os, Mo, Ag, Au, alloys thereof, and combinations thereof.

The acid condensation catalyst may be self-supporting (i.e., the catalyst does not need another material to serve as a support), or may require a separate support suitable for suspending the catalyst in the reactant stream, such as any one of the supports further described below, including supports containing carbon, silica, alumina, zirconia, titania, vanadia, kieselguhr, hydroxyapatite, chromia, mixtures thereof, and combinations thereof. In some embodiments, particularly when the acid condensation catalyst is a powder, the catalyst system may include a binder to assist in forming the catalyst into a desirable catalyst shape. Applicable binders include, without limitation alumina, clay, silica, zinc aluminate, aluminum phosphate, and zirconia. Numerous forming processes may be employed to produce the catalyst including extrusion, pelletization, oil dropping, or other known processes. After drying, this material is calcined at a temperature appropriate for formation of the catalytically active phase, which usually requires temperatures in excess of 400° C.

The acid condensation catalyst may include one or more zeolite structures comprising cage-like structures of silica-alumina. Zeolites are crystalline microporous materials with a well-defined pore structure. Zeolites also contain active sites, usually acid sites, which can be generated in the zeolite framework, the strength and concentration of which can be tailored for particular applications. The structure of the particular zeolite or zeolites may also be altered to produce different amounts of various hydrocarbon species in the product mixture. For example, the zeolite catalyst may be structured to produce a product mixture contain various amounts of cyclic hydrocarbons. Ga, In, Zn, Fe, Mo, Ag, Au, Ni, P, Sc, Y, Ta, and lanthanides may also be exchanged onto zeolites to provide a zeolite catalyst having a particular desired activity. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof. Accordingly, "zeolites" not only refers to microporous crystalline aluminosilicate, but also to microporous crystalline metal-containing aluminosilicate structures, such as galloaluminosilicates and gallosilicates.

The acid condensation catalyst may also be a bifunctional pentasil zeolite catalyst including at least one metallic element from the group of Re, Cu, Fe, Ru, Ir, Co, Rh, Pt, Pd, Ni, W, Os, Mo, Ag, Au, Sn, alloys and combinations thereof, or a modifier from the group of Ga, In, Zn, Fe, Mo, Au, Ag, Y, Sc, Ni, P, Ta, lanthanides, and combinations thereof. The zeolite preferably has a strong acidic and dehydrogenation sites, and may be used with reactant streams containing an oxygenated hydrocarbon at a temperature of below 500° C.

The bifunctional pentasil zeolite may have ZSM-5, ZSM-8 or ZSM-11 type crystal structure consisting of a large number of 5-membered oxygen containing-rings, i.e., pentasil rings. The zeolite with ZSM-5 type structure is a particularly preferred catalyst. The bifunctional pentasil zeolite catalyst may be a Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. The bifunctional ZSM-5 type pentasil zeolite may contain tetrahedral aluminum and/or gallium present in the zeolite framework or lattice and octahedral gallium or indium. The octahedral sites are not present in the zeolite framework but are present in the zeolite channels in a close vicinity of the zeolitic protonic acid sites, which are attributed to the presence of tetrahedral aluminum and gallium in the zeolite. The tetrahedral or framework Al and/or Ga is believed to be responsible for the acid function of the zeolite, and octahedral or non-framework Ga and/or In is believed to be responsible for the dehydrogenation function of the zeolite.

Examples of other suitable zeolite catalysts include ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference.

Alternatively, solid acid catalysts such as alumina modified with phosphates, chloride, silica, and other acidic oxides could be used as an acid condensation catalyst in practicing the present invention. Sulfated zirconia or tungstated zirconia may also provide the necessary acidity. In one embodiment, the acid condensation catalyst is tungstated zirconia modified to have at least one metallic element from the group of Re, Cu, Fe, Ru, Ir, Co, Rh, Pt, Pd, Ni, W, Os, Mo, Ag, Au, alloys and combinations thereof.

The acid condensation catalyst may also be a resin capable of serving as an acidic support (e.g., supports having low isoelectric points) that are able to catalyze condensation reactions. Heteropolyacids are a class of solid-phase acids exemplified by such species as $H_{3+x}PMO_{12-x}V_xO_{40}$, $H_4SiW_{12}O_{40}$, $H_3PW_{12}O_{40}$, and $H_6P2W_{18}O_{62}$. Heteropolyacids also have a well-defined local structure, the most common of which is the tungsten-based Keggin structure.

The specific $C_{8+}$ compounds produced will depend on various factors, including, without limitation, the make-up of the reactant stream, the type of oxygenates in the first reactant, the hydrocarbons and oxygenated hydrocarbons in the second reactant, the concentration of the water, condensation temperature, condensation pressure, the reactivity of the catalyst, and the flow rate of the reactant stream as it affects the space velocity (the mass/volume of reactant per unit of catalyst per unit of time), gas hourly space velocity (GHSV), and weight hourly space velocity (WHSV). Preferably, the reactant stream is contacted with the acid condensation catalyst at a WHSV that is appropriate to produce the desired hydrocarbon products. The WHSV is preferably at least about 0.1 grams of oxygenate in the reactant stream per hour, more preferably the WHSV is between about 0.1 to 40.0 g/g hr, including a WHSV of about 0.2, 0.4, 0.6, 0.8, 1, 2, 3, 4, 5, 6, 7, 8, 9, 10, 11, 12, 13, 14, 15, 20, 25, 30, 35 g/g hr, and increments between.

The condensation temperature and pressure conditions may be selected to more favorably produce the desired products in the vapor-phase or in a mixed phase having both a liquid and vapor phase. In general, the condensation reaction should be conducted at a temperature and pressure where the thermodynamics of the reactions are favorable. For instance, the minimum pressure required to maintain a portion of the reactant stream in the liquid phase will vary with the reaction temperature. As temperatures increase, higher pressures will generally be required to maintain the reactant stream in the liquid phase. Any pressure above that required to maintain the feedstock in the liquid phase (i.e., vapor-phase) is also a suitable operating pressure. For vapor phase reactions, the reaction should be conducted at a condensation temperature where the vapor pressure of the oxygenated hydrocarbon compound is at least about 0.1 atm (and preferably a good deal higher), and the thermodynamics of the reactions are favorable.

In general, the condensation temperature should be greater than 100° C., or 150° C., or 180° C., or 200° C., and less than 500° C., or 400° C., or 370° C., or 350° C. The reaction pressure should be greater than 72 psig, or 125 psig, or 200 psig, or 300 psig, or 365 psig, or 500 psig, and less than 2000 psig, or 1800 psig, or 1700 psig, or 1500 psig. In one embodiment, the condensation temperature is between about 100° C. and 400° C., or between about 150° C. and 370° C., or between about 180° C. and 300° C. In another embodiment, the deoxygenation pressure is between about 72 and 2000 psig, or between about 200 and 1800 psig, or between about 300 and 1700 psig, or between about 500 and 1500 psig.

Varying the factors above, as well as others, will generally result in a modification to the specific composition and yields of the $C_{8+}$ compounds. For example, varying the temperature and/or pressure of the reactor system, or the particular catalyst formulations, may result in the production of more $C_{8+}$ alcohols and/or ketones instead of $C_{8+}$ hydrocarbons. Varying the temperature and/or pressure of the reactor system, or the particular catalyst formulations, may also result in the production of $C_{7-}$ compounds which may be recycled and used as the second reactant or used for liquid fuels (e.g., gasoline) or chemicals, either directly or after further processing.

The $C_{8+}$ product compounds may contain high levels of alkenes, alcohols and/or ketones, which may be undesirable in certain fuel applications or which lead to coking or deposits in combustion engines, or other undesirable combustion products. In such event, the $C_{8+}$ compounds may be optionally hydrogenated to reduce the ketones to alcohols and hydrocarbons, and the alcohols and unsaturated hydrocarbons to alkanes, cycloalkanes, and aryls, thereby forming a more desirable hydrocarbon product having low levels of alkenes, alcohols or ketones.

The $C_{8+}$ compounds product may also undergo a finishing step. The finishing step will generally be a hydrotreating reaction that removes a portion of the remaining carbon-carbon double bonds, carbonyl, hydroxyl, acid, ester, and ether groups. In such event, any one of several hydrotreating catalysts described may be used. Such catalysts may include any one or more of the following metals, Cu, Ni, Fe, Co, Mo, W, Ru, Pd, Rh, Pt, Ir, alloys or combinations thereof, alone or with promoters such as Au, Ag, Cr, Zn, Mn, Sn, Cu, Bi, and alloys thereof, may be used in various loadings ranging from about 0.01 to about 20 wt % on a support as described above.

In general, the finishing step is carried out at finishing temperatures of between about 80° C. to 400° C., and finishing pressures in the range of about 100 psig to 2000 psig. The finishing step may be conducted in the vapor phase or liquid phase, and may use in situ generated $H_2$, external $H_2$, recycled $H_2$, or combinations thereof, as necessary.

Other factors, such as the concentration of water or undesired oxygenates, may also affect the composition and yields of the $C_{8+}$ compounds. In such event, the process may include a dewatering step that removes a portion of the water after condensation or a separation unit for removal of the undesired oxygenates. For instance, a separator unit, such as a phase separator, extractor, purifier or distillation column, may be installed after the condensation step so as to remove a portion of the water from the product stream. A separation unit may also be installed to remove specific oxygenates for recycle and use as the first reactant or as a supplement to the first reactant, and/or hydrocarbons and oxygenated hydrocarbons for use as the second reactant or as a supplement to the second reactant.

$C_{8+}$ Compounds

The present invention allows for the production of a higher yield of $C_{8+}$ compounds due to the unique combination of the first and second reactants in the reactant stream. In one embodiment, the yield of $C_{8+}$ compounds in the product stream is greater than 40%, or greater than 50%, or greater than 60%, or greater than 75% of the carbon yield for the product stream. In another embodiment, the yield of $C_{8+}$ compounds in the heavy portion of the product stream is greater than 60%, or greater than 70%, or greater than 80%, or greater than 90%, or greater than 95% of the carbon in the heavy portion of the product stream. In yet another embodiment, the yield of $C_{8+}$ compounds in the product stream is more than 10%, or more then 25%, or more then 50%, or more then 75%, or more then 100%, or more than 150%, or more than 200% greater than the practice of the invention without the inclusion of a second reactant stream.

The condensation reactions result in the production of $C_{8+}$ alkanes, $C_{8+}$ alkenes, $C_{8+}$ cycloalkanes, $C_{8+}$ cycloalkenes, $C_{8+}$ aryls, fused aryls, $C_{8+}$ alcohols, $C_{8+}$ ketones, oxygenated $C_{8+}$ aryls, oxygenated fused aryls, and mixtures thereof. The $C_{8+}$ alkanes and $C_{8+}$ alkenes have 8 or more carbon atoms, and may be branched or straight chained alkanes or alkenes. The $C_{8+}$ alkanes and $C_{8+}$ alkenes may also include fractions containing $C_8$, $C_9$, $C_{10}$, $C_{11}$, $C_{12}$, $C_{13}$, $C_{14}$ compounds ($C_{8-14}$ fraction), or $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$ compounds ($C_{12-24}$ fraction), or more than 25 carbon atoms ($C_{25+}$ fraction), with the $C_{8-14}$ fraction directed to jet fuels, the $C_{12-24}$ fraction directed to diesel fuel, and the $C_{25+}$ fraction directed to heavy oils and other industrial applications. Examples of various $C_{8+}$ alkanes and $C_{8+}$ alkenes include, without limitation, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{8+}$ cycloalkanes and $C_{8+}$ cycloalkenes have 8 or more carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a straight chain $C_{2+}$ alkyne, a phenyl or a combination thereof. In one embodiment, at least one of the substituted groups include a branched $C_{3+}$ alkyl, a straight chain $C_{1+}$ alkyl, a branched $C_{3+}$ alkylene, a straight chain $C_{2+}$ alkylene, a straight chain $C_{2+}$ alkyne, a phenyl or a combination thereof. Examples of desirable $C_{8+}$ cycloalkanes and $C_{8+}$ cycloalkenes include, without limitation, ethyl-cyclopentane, ethyl-cyclopentene, ethyl-cyclohexane, ethyl-cyclohexene, and isomers thereof.

The $C_{8+}$ aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. Examples of various $C_{8+}$ aryls include, without limitation, xylene (dimethylbenzene), ethyl benzene, para xylene, meta xylene, ortho xylene, $C_9$ aromatics (such as trimethyl benzene, methyl ethyl benzene, propyl benzene), and $C_{10}$ aromatics (such as diethylbenzene, tetramethylbenzene, dimethyl ethylbenzene), etc.

Fused aryls will generally consist of bicyclic and polycyclic aromatic hydrocarbons, in either an unsubstituted, mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, tetrahydronaphthalene, and decahydronaphthalene, indane, indene, and isomers thereof.

The $C_{8+}$ alcohols may also be cyclic, branched or straight chained, and have 8 or more carbon atoms. In general, the $C_{8+}$ alcohols may be a compound according to the formula $R^1$—OH, wherein $R^1$ is a member selected from the group consisting of a branched $C_{8+}$ alkyl, straight chain $C_{8+}$ alkyl, a branched $C_{8+}$ alkylene, a straight chain $C_{8+}$ alkylene, a substituted $C_{8+}$ cycloalkane, an unsubstituted $C_{8+}$ cycloalkane, a substituted $C_{8+}$ cycloalkene, an unsubstituted $C_{8+}$ cycloalkene, an aryl, a phenyl and combinations thereof. Examples of desirable $C_{8+}$ alcohols include, without limitation, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{8+}$ ketones may also be cyclic, branched or straight chained, and have 8 or more carbon atoms. In general, the $C_{8+}$ ketone may be a compound according to the formula

$$\begin{array}{c} R^3 \\ \diagdown \\ C=O \\ \diagup \\ R^4 \end{array}$$

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and a combination thereof. Examples of desirable $C_{8+}$ ketones include, without limitation, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Oxygenated $C_{8+}$ aryls will generally consist of an aromatic hydrocarbon (in either an unsubstituted (phenyl), mono-substituted or multi-substituted form) having one or more oxygen atoms. Examples of oxygenated $C_{8+}$ aryls include, without limitation, $C_{8+}$ alkyl substituted phenols, alkyl substituted indanones, alkyl substituted benzoic acids, alkyl substituted aryl alcohols, alkyl substibuted aryl aldehydes, terephthalic acid, isophthalic acid, Oxygenated fused aryls will generally consist of bicyclic and polycyclic aromatic hydrocarbons (in either an unsubstituted, mono-substituted or multi-substituted form) having one or more oxygen atoms. Examples of oxygenated fused aryls include, without limitation, alkyl substituted naphthols, alkyl substituted naphthalenic acids, alkyl substituted naphthalenic alcohols, alkyl substibuted naphthalenic aldehydes, and 2,6 naphthalenedicarboxylic acid.

The moderate fractions above ($C_8$-$C_{14}$) may be separated for jet fuel, while the $C_{12}$-$C_{24}$ fraction may be separated for diesel fuel, and the heavier fraction ($C_{25+}$) separated for use as a heavy oil or cracked to produce additional gasoline and/or diesel fractions. The $C_{8+}$ compounds may also be used as industrial chemicals, whether as an intermediate or an end product. For example, the $C_9$ aromatics and fused aryls, such as naphthalene, tetrahydronaphthalene, decahydronaphthalene, and anthracene may be used as solvents in industrial processes.

$C_{7-}$ Compounds

The condensation reactions will also result in the production of $C_{7-}$ alkanes, $C_{7-}$ alkenes, $C_{7-}$ cycloalkanes, $C_{7-}$ cycloalkenes, $C_{7-}$ alcohols, $C_{7-}$ ketones, $C_{7-}$ aryls, and mixtures thereof. Preferably, the $C_{7-}$ compounds are of the type appropriate for use as the second reactant or as a supplement to the second reactant. Accordingly, in one embodiment, the $C_{7-}$ compounds may be separated from the product stream and recycled for use as the second reactant. In another embodiment, a portion of the $C_{7-}$ compounds may be separated from the product stream and used as a gasoline or as blending component for gasoline, or in other industrial applications.

In general, the $C_{7-}$ alkanes and $C_{7-}$ alkenes have from 4 to 7 carbon atoms ($C_{4-7}$ alkanes and $C_{4-7}$ alkenes) and may be cyclic, branched or straight chained alkanes or alkenes. Examples of various $C_{7-}$ alkanes and $C_{7-}$ alkenes include, without limitation, butane, iso butane, butene, isobutene, pentane, pentene, 2-methylbutane, hexane, hexene, 2-methylpentane, 3-methylpentane, 2,2-dimethylbutane, 2,3-dimethylbutane, cyclohexane, heptane, heptene, methyl-cyclohexane and isomers thereof.

The $C_{7-}$ alcohols may also be cyclic, branched or straight chained, and have 7 or less carbon atoms. In general, the $C_{7-}$ alcohols may be a compound according to the formula $R^5$—OH, wherein $R^5$ is a member selected from the group consisting of a branched $C_{7-}$ alkyl, straight chain $C_{7-}$ alkyl, a branched $C_{7-}$ alkylene, a straight chain $C_{7-}$ alkylene, a substituted $C_{7-}$ cycloalkane, an unsubstituted $C_{7-}$ cycloalkane, a substituted $C_{7-}$ cycloalkene, an unsubstituted $C_{7-}$ cycloalkene, a $C_{7-}$ aryl, a $C_{7-}$ phenyl and combinations thereof. Examples of desirable $C_{7-}$ alcohols include, without limitation, ethanol, 1-propanol, isopropanol, 1-butanol, 2-butanol, isobutanol, tert-butyl alcohol, pentanol, hexanol, heptanol, and isomers thereof.

The $C_{7-}$ ketones may also be cyclic, branched or straight chained, and have 7 or less carbon atoms. In general, the $C_{7-}$ ketone may be a compound according to the formula

$$R^3=O$$

wherein $R^3$ is a member selected from the group consisting of a branched $C_{3-7}$ alkyl, a straight chain $C_{3-7}$ alkyl, a branched $C_{3-7}$ alkylene, a straight chain $C_{3-7}$ alkylene, a substituted $C_{5-}$ cycloalkane, cyclopentane, methyl-cyclopentane, cyclohexane, and combinations thereof. Examples of desirable $C_{7-}$ ketones include, without limitation, acetone, butanone, 2-pentanone, 3-pentanone, 3-methyl-butan-2-one, 2-hexanone, 3-hexanone, 3-methyl-pentyl-2-one, 4-methyl-pentyl-2-one, 2-methyl-pentyl-3-one, 2-heptanone, 3-heptanone, 4-heptanone, cyclopentanone, methyl-cyclopentanone, 2-methyl-cyclopentanone, 3-methyl-cyclopentanone, cyclohexanone, and isomers thereof.

The $C_{7-}$ aryls will generally consist of an aromatic hydrocarbon having 6 or 7 carbon atoms, whether in either an unsubstituted (phenyl), mono-substituted or multi-substituted form. Examples of various aryls include benzene and toluene.

The $C_{7-}$ cycloalkanes and $C_{7-}$ cycloalkenes have 5, 6 or 7 carbon atoms and may be unsubstituted, mono-substituted or multi-substituted. In the case of mono-substituted and multi-substituted compounds, the substituted group may include a, a straight chain $C_{1-2}$ alkyl, a straight chain $C_2$ alkylene, a straight chain $C_2$ alkyne, or a combination thereof. Examples of desirable $C_{7-}$ cycloalkanes and $C_{7-}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, and isomers thereof.

Biomass Derived Feedstocks

As used herein, the term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled paper, waste paper and yard clippings; and (4) energy crops, including poplars, willows, switch grass, miscanthus, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

As used herein, the term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, diols and other polyols, using aqueous phase reforming, hydrogenation, hydrogenolysis, hydrodeoxygenation and/or other conversion processes involving the use of heterogeneous catalysts. Bioreforming also includes the further catalytic conversion of such lower molecular weight oxygenated compounds to $C_{4+}$ compounds.

As used herein, the term "biomass-derived feedstock" refers to, without limitation, materials which originate from biomass and which has use as a feedstock in one or more bioreforming processes. Preferably, the biomass-derived feedstock is derived from material of recent biological origin such that the age of the compounds, or fractions containing the compounds, is less than 100 years old, preferably less than 40 years old, and more preferably less than 20 years old, as calculated from the carbon 14 concentration of the feedstock. Common biomass-derived feedstocks include lignin and lignocellulosic derivatives, cellulose and cellulosic derivatives, hemicellulose and hemicellulosic derivatives, carbohydrates, starches, monosaccharides, disaccharides, polysaccharides, sugars, sugar alcohols, alditols, polyols, and mixtures thereof. Preferably, the biomass biomass-derived feedstock includes a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, arabitol, glycol, and other oxygenated hydrocarbons.

"Oxygenated hydrocarbons" refers to hydrocarbon compounds having the general formula $C_aH_bO_d$, wherein a represents two or more carbon atoms and d represents at least one oxygen atom (collectively, referred to herein as $C_{2+}O_{1+}$ hydrocarbons). Preferably, the oxygenated hydrocarbon has 2 to 12 carbon atoms ($C_{2-12}O_{1-11}$ hydrocarbon), and more preferably 2 to 6 carbon atoms ($C_{2-6}O_{1-6}$ hydrocarbon). The oxygenated hydrocarbon may also have an oxygen-to-carbon ratio ranging from 0.07 to 1.0, including ratios of 0.08, 0.09, 0.10, 0.16, 0.20, 0.25, 0.3, 0.33, 0.4, 0.5, 0.6, 0.7, 0.75, 0.8, 0.9, and other ratios between. Additional nonlimiting examples of oxygenated hydrocarbons include various alcohols, ketones, aldehydes, furans, hydroxy carboxylic acids, carboxylic acids, diols and triols. Alcohols may include, without limitation, primary, secondary, linear, branched or cyclic $C_{2+}$ alcohols, such as ethanol, n-propyl alcohol, isopropyl alcohol, butyl alcohol, isobutyl alcohol, butanol, isobutanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, and isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane (trimethylolethane), trimethylolpropane, hexanetriol, and isomers thereof. Cyclic ethers, furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl) ethanol, hydroxymethyltetrahydrofurfural, and isomers thereof.

The biomass-derived feedstock may be produced by any known method. Such methods include deconstruction technologies using enzymes or microorganisms, Fischer-Tropsch reactions to produce $C_{2-10}$ alpha alcohols, fermentation technologies using enzymes or microorganisms, and pyrolysis technologies to produce alcohols from oil, among others. In one embodiment, the biomass-derived feedstock is produced using a catalytic reforming technology, such as those described in U.S. Pat. Nos. 7,767,867; 7,989,664; and 8,198,486; and U.S. Application No. 2012/0283478 (all to Cortright, and entitled "Methods and Systems for Generating Polyols"). Various APR and HDO methods and techniques are described in U.S. Pat. Nos. 8,053,615; 8,017,818; 7,977,517; 8,362,307; 8,367,882; and U.S. Patent Application Ser. Nos. 2011/0245542 and 2011/0257448 (all to Cortright and Blommel, and entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Pat. No. 8,350,108 (to Cortright et al., and entitled "Synthesis of Liquid Fuels from Biomass"); U.S. patent application Ser. No. 13/586,499 (to Blank et al. and entitled "Improved Catalysts for the Hydrodeoxygenation of Oxygenated Hydrocarbons"); International Patent Application No. PCT/US2008/056330 (to Cortright and Blommel, and entitled "Synthesis of Liquid Fuels and Chemicals from Oxygenated Hydrocarbons").

Production of Oxygenates

The first reactant stream can be provided by reacting an aqueous feedstock solution containing water and one or more water-soluble oxygenated hydrocarbons with hydrogen over a catalytic material to produce a first reactant stream containing water and oxygenates. The hydrogen may be generated in situ using aqueous phase reforming (APR $H_2$), or a combination of APR $H_2$, external $H_2$ or recycled $H_2$, or just simply external $H_2$ or recycled $H_2$.

In processes utilizing APR $H_2$, the oxygenates are prepared by catalytically reacting a first portion of the aqueous feedstock solution containing water and the water-soluble oxygenated hydrocarbons in the presence of an APR catalyst at a reforming temperature and reforming pressure to produce the APR $H_2$, and catalytically reacting the APR $H_2$ (and recycled $H_2$ and/or external $H_2$) with a second portion of the feedstock solution in the presence of a deoxygenation catalyst at a deoxygenation temperature and deoxygenation pressure to produce the desired oxygenates for the first reactant stream. In systems utilizing recycled $H_2$ or external $H_2$ as a hydrogen source, the oxygenates are simply prepared by catalytically reacting the recycled $H_2$ and/or external $H_2$ with the aqueous feedstock solution in the presence of the deoxygenation catalyst at the deoxygenation temperatures and pressures.

The deoxygenation catalyst is preferably a heterogeneous catalyst having one or more active materials capable of catalyzing a reaction between hydrogen and the oxygenated hydrocarbon to remove one or more of the oxygen atoms from the oxygenated hydrocarbon to produce alcohols, ketones, aldehydes, cyclic ethers, carboxylic acids, hydroxy carboxylic acids, diols, triols, and mixtures thereof. Mixtures of the oxygenates include mixtures of compounds within a class (i.e., a mixture of alcohols including butanol, propanol and hexanol) as well as mixtures of classes (i.e., a mixture of diols and carboxylic acids including ethylene glycol, propylene glycol, propionic acid, and acetic acid). In general, the heterogeneous deoxygenation catalyst will have both an active metal function and an acidic function to achieve the foregoing. For example, acidic supports first catalyze dehydration reactions of oxygenated compounds. Hydrogenation reactions then occur on the metallic catalyst in the presence of $H_2$, producing carbon atoms that are not bonded to oxygen atoms. The bi-functional dehydration/hydrogenation pathway consumes $H_2$ and leads to the subsequent formation of various polyols, diols, ketones, aldehydes, alcohols, carboxylic acids, hydroxy carboxylic acids and cyclic ethers, such as furans and pyrans. In one embodiment, the deoxygenation catalyst is atomically identical to the acid condensation catalyst.

The active materials may include, without limitation, Cu, Re, Fe, Ru, Ir, Co, Rh, Pt, Pd, Ni, W, Os, Mo, Ag, Au, alloys thereof, and combinations thereof, adhered to a support. The deoxygenation catalyst may include these elements alone or in combination with one or more Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof. In one embodiment, the deoxygenation catalyst includes Pt, Pd, Ru, Re, Ni, W or Mo. In yet another embodiment, the deoxygenation catalyst includes Sn, W, Mo, Ag, Fe and/or Re and at least one transition metal selected from Ni, Pd, Pt and Ru. In another embodiment, the catalyst includes Fe, Re and at least Cu or one Group VIIIB transition metal. In yet another embodiment, the deoxygenation catalyst includes Pd alloyed or admixed with Cu or Ag and supported on an acidic support. In yet another embodiment, the deoxygenation catalyst includes Pd alloyed or admixed with a Group VIB metal supported on an acidic support. In yet another embodiment, the deoxygenation catalyst includes Pd alloyed or admixed with a Group VIB metal and a Group IVA metal on an acidic support. The support may be any one of a number of supports, including a support having carbon, silica, alumina, zirconia, titania, tungsten, vanadia, chromia, zeolites, heteropolyacids, kieselguhr, hydroxyapatite, and mixtures thereof.

The deoxygenation catalyst may also include an acidic support modified or constructed to provide the desired functionality. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids are solid-phase acids having a well-defined local structure, the most common of which is the tungsten-based Keggin structure. Other examples may include, without limitation, tungstated zirconia, tungsten modified zirconia, alpha alumina, theta alumina, tungsten modified alpha-alumina, or tungsten modified theta alumina.

Loading of the first element (i.e., Cu, Re, Fe, Ru, Ir, Co, Rh, Pt, Pd, Ni, W, Os, Mo, Ag, Au, alloys and combinations thereof) is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second element (i.e., Mn, Cr, Mo, W, V, Nb, Ta, Ti, Zr, Y, La, Sc, Zn, Cd, Ag, Au, Sn, Ge, P, Al, Ga, In, Tl, Ce, and combinations thereof) is in the range of 0.25-to-1 to 10-to-1, including any ratios between, such as 0.50, 1.00, 2.50, 5.00, and 7.50-to-1. If the catalyst is adhered to a support, the combination of the catalyst and the support is from 0.25 wt % to 10 wt % of the primary element.

To produce oxygenates, the oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also include recycled oxygenated hydrocarbons recycled from the reactor system. The feedstock solution may also contain negligible amounts of hydrogen, preferably less than about 1.5 mole of hydrogen per mole of feedstock.

The feedstock solution is reacted with hydrogen in the presence of the deoxygenation catalyst at deoxygenation temperature and pressure conditions and weight hourly space velocity effective to produce the desired oxygenates. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity, GHSV, and WHSV. For example, an increase in flow rate, and thereby a reduction of feedstock exposure to the catalysts over time, will limit the extent of the reactions which may occur, thereby causing increased yield for higher level diols and triols, with a reduction in ketone and alcohol yields.

The deoxygenation temperature and pressure are preferably selected to maintain at least a portion of the feedstock in the liquid phase at the reactor inlet. It is recognized, however, that temperature and pressure conditions may also be selected to more favorably produce the desired products in the vapor-phase or in a mixed phase having both a liquid and vapor phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the deoxygenation temperature should be greater than 80° C., or 120° C., or 150° C., or 180° C., or 200° C., and less than 500° C., or 450° C., or 325° C., or 300° C., or 280° C., or 260° C., or 240° C., or 220° C. The reaction pressure should be greater than 200 psig, or 365 psig, or 500 psig or 600 psig, and less than 2500 psig, or 2250 psig, or 2000 psig, or 1800 psig, or 1500 psig, or 1200 psig, or 1000 psig, or 725 psig. In one embodiment, the deoxygenation temperature is between about 150° C. and 300° C., or between about 200° C. and 280° C., or between about 220° C. and 260° C., or between about 150° C. and 260° C. In another embodiment, the deoxygenation pressure is between about 365 and 2500 psig, or between about 500 and 2000 psig, or between about 600 and 1800 psig, or between about 365 and 1500 psig.

A condensed liquid phase method may also be performed using a modifier that increases the activity and/or stability of the catalyst system. For example, alkali or alkali earth salts may be added to optimize the system. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

In general, the reaction should be conducted under conditions where the residence time of the feedstock solution over the catalyst is appropriate to generate the desired products. For example, the WHSV for the reaction may be at least about 0.1 gram of oxygenated hydrocarbon per gram of catalyst per hour, and more preferably the WHSV is about 0.01 to 40.0 g/g hr, including a WHSV of about 0.05, 0.1, 0.25, 0.5, 0.75, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.83, 0.85, 0.85, 1.71, 1.72, 1.73, etc.).

The hydrogen used in the deoxygenation reaction may be in-situ-generated $H_2$, external $H_2$ or recycled $H_2$. The amount (moles) of external $H_2$ or recycled $H_2$ introduced to the feedstock is between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external $H_2$ or recycled $H_2$, the molar ratio of APR hydrogen to external $H_2$ (or recycled $H_2$) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

In-Situ Hydrogen Production

One advantage of the present invention is that it allows for the production and use of in-situ-generated $H_2$. The APR $H_2$ is produced from the feedstock under aqueous phase reforming conditions using an aqueous phase reforming catalyst (APR catalyst). The APR catalyst is preferably a heterogeneous catalyst capable of catalyzing the reaction of water and oxygenated hydrocarbons to form $H_2$ under the conditions described below. In one embodiment, the APR catalyst includes a support and at least one of, Fe, Ru, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA or Group VA metals, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys and combinations thereof. The preferred Group VIIB metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the catalyst supports described below, depending on the desired activity of the catalyst system.

The APR catalyst may also be atomically identical to the deoxygenation catalyst or combined to form a single catalyst. The combined APR/deoxygenation catalyst may also be atomically identical to the acid condensation catalyst. For instance, the APR and deoxygenation catalyst may include Pt alloyed or admixed with Ni, Ru, Cu, Fe, Rh, Re, alloys and combinations thereof. The APR catalyst and deoxygenation catalyst may also include Ru alloyed or admixed with Ge, Bi, B, Ni, Sn, Cu, Fe, Rh, Pt, alloys and combinations thereof. The APR catalyst and deoxygenation catalyst may also include Pd alloyed or admixed with Ni, Ag, Au, Sn, Cu, Mo, Fe, Rh, Pt, alloys and combinations thereof. The APR catalyst may also include Ni alloyed or admixed with Sn, Ge, Bi, B, Cu, Re, Ru, Fe, alloys and combinations thereof.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

A preferred catalyst composition is further achieved by the addition of oxides of Group IIIB and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another preferred catalyst composition is one containing platinum and rhenium. The preferred atomic ratio of Pt to Re is in the range of 0.25-to-1 to 10-to-1, including ratios there-between, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

Preferably, the APR catalyst and the deoxygenation catalyst are of the same atomic formulation. The catalysts may also be of different formulations. The catalysts may also be a single catalyst with both APR and deoxygenation functionality provided by the combination of the above described APR materials and deoxygenation materials. In such event, the preferred atomic ratio of the APR catalyst to the deoxygenation catalyst is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts between.

Similar to the deoxygenation reactions, the temperature and pressure conditions are preferably selected to maintain at least a portion of the feedstock in the liquid phase at the reactor inlet. The reforming temperature and pressure conditions may also be selected to more favorably produce the desired products in the vapor-phase or in a mixed phase having both a liquid and vapor phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reforming temperature may be from about 80° C. to 400° C., and the reforming pressure from about 72 psig to 1300 psig.

In one embodiment, the reforming temperature is between about 100° C. and 400° C., or between about 120° C. and 300° C., or between about 200° C. and 280° C., or between about 150° C. and 270° C. The reforming pressure is preferably between about 72 and 1300 psig, or between about 72 and 1200 psig, or between about 145 and 1200 psig, or between about 200 and 725 psig, or between about 365 and 700 psig, or between about 600 and 650 psig.

In embodiments where the APR catalyst and the deoxygenation catalyst are combined into a single catalyst, or the reactions are conducted simultaneously in a single reactor, the reforming temperature and deoxygenation temperature may be in the range of about 100° C. to 325° C., or about 120° C. to 300° C., or about 200° C. to 280° C., and the reforming pressure and deoxygenation pressure may be in the range of about 200 psig to 1500 psig, or about 200 psig to 1200 psig, or about 200 psig to 725 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products in the hydrogenation reactions described below. It is preferred that the water-soluble acid is selected from the group consisting of nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the deoxygenation catalyst to provide the desired oxygenates. For example, the WHSV for the reaction may be at least about 0.01 gram of oxygenated hydrocarbon per gram of APR catalyst, and preferably between about 0.1 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Reactor System

The reactions described herein may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. Preferably, the present invention is practiced utilizing a continuous-flow system at steady-state equilibrium.

In a continuous flow system, the reactor system includes at least a reforming bed adapted to receive an aqueous feedstock solution to produce hydrogen, a deoxygenation bed adapted to produce oxygenates from the hydrogen and a portion of the feedstock solution, and a condensation bed adapted to produce $C_{8+}$ compounds from hydrogen, the oxygenates and a portion of a second reactant. The reforming bed is configured to contact the aqueous feedstock solution in a vapor phase or liquid phase with the APR catalyst to provide hydrogen in a reactant stream. The deoxygenation bed is configured to receive to contact a portion of the aqueous feedstock with hydrogen and the deoxygenation catalyst to produce water and the desired oxygenates. The condensation bed is configured to receive a reactant stream containing the water and oxygenates as a first reactant and the second reactant, and then contacting the reactant stream with hydrogen and the acid condensation catalyst to produce a product stream containing the desired $C_{8+}$ compounds. For systems not involving an APR hydrogen production step, the reforming bed may be removed. For systems not involving a hydrogen or oxygenate production step, the reforming and deoxygenation beds may be removed. Because the APR catalyst, deoxygenation catalyst and condensation catalyst may also be atomically identical, the catalysts may exist as the same bed. For systems with a finishing step, an additional reaction bed for conducting the finishing process may be included after the condensation bed. For systems involving a recycle stream that provides the second reactant, an additional separation system for separating the water and the recycle stream from the desired $C_{8+}$ compounds may be included after the condensation bed. The water separation unit and recycle stream separation unit may be separate systems or combined into a single separation system.

In systems producing both hydrogen and oxygenates, the deoxygenation bed may be positioned within the same reactor vessel along with the reforming bed or in a second reactor vessel in communication with a first reactor vessel having the reforming bed. The condensation bed may be within the same reactor vessel along with the reforming or deoxygenation bed or in a separate reactor vessel in communication with the reactor vessel having the deoxygenation bed. Each reactor vessel preferably includes an outlet adapted to remove the product stream from the reactor vessel. For systems with a finishing step, the finishing reaction bed may be within the same reactor vessel along with the condensation bed or in a separate reactor vessel in communication with the reactor vessel having the condensation bed.

The reactor system may also include additional outlets to allow for the removal of portions of the product stream to further advance or direct the reaction to the desired reaction products, and to allow for the collection and recycling of the $C_{7-}$ products for use as the second reactant or other reaction byproducts for use in other portions of the system. The reactor system may also include additional inlets to allow for the introduction of supplemental materials to further advance or direct the reaction to the desired reaction products, and to allow for the recycling of the $C_{7-}$ products for use as the second reactant or other reaction byproducts for use in the process. For example, the system may be designed such that excess hydrogen is produced over the APR catalyst, with a portion of the excess hydrogen removed and reintroduced downstream to the condensation reaction or the finishing of the condensation product to arrive at the desired $C_{8+}$ compounds. Alternatively, the system may be designed such that excess hydrogen is produced over the APR catalyst, with a portion of the excess hydrogen removed and used in other upstream processes, such as feedstock pretreatment processes and hydrogenation or hydrogenolysis reactions.

The reactor system may also include elements which allow for the separation of the reactant stream into different components which may find use in different reaction schemes or to simply promote the desired reactions. For instance, a separator unit, such as a phase separator, extractor, purifier or distillation column, may be installed after the condensation step to remove water from the product stream for purposes of assisting in the separation of the $C_{8+}$ compounds from the $C_{7-}$ compounds and the collection of the $C_{7-}$ compounds for use as a portion of the second reactant. A separator unit may also be installed prior to the condensation step to remove water from the reactant stream for purposes of advancing the condensation reaction to favor the production of the desired hydrocarbons. A separation unit may also be installed to remove specific oxygenates to allow for the production of a desired product stream containing hydrocarbons within a particular carbon range or for use as end products or in other systems or processes.

EXAMPLES

Illustrative Reactor Systems

Example 1

FIG. 1 shows a process diagram illustrating one reactor system useful in practicing the present invention. A first reactant stream containing water and oxygenated intermediates, such as alcohols, ketones, cyclic ethers, organic acids, or other poly-oxygenated compounds, is provided by stream 202. The first reactant stream is combined with hydrogen 301 and a second reactant stream 408 containing light hydrocarbons and mono-oxygenated hydrocarbons derived from the process.

The combined reactant stream is directed through Condensation Reactor 204 where the reactants catalytically react with an acid condensation catalyst at a condensation temperature and condensation pressure to form product stream 206 containing primarily hydrocarbons, mono-oxygenated hydrocarbons, and water. The chain length of the hydrocarbons and mono-oxygenated hydrocarbons vary from $C_3$-$C_{30}$ depending on the extent of condensation.

Product stream 206 is sent to a separation unit 400 (Lights Recycle Column) to yield a heavy fraction 411 containing $C_{8+}$ hydrocarbons and oxygenated hydrocarbons, and a lighter fraction 402 containing water and $C_{7-}$ hydrocarbons and oxygenated hydrocarbons. The lighter fraction 402 is separated from the heavy fraction and directed to a three phase separator 410 to provide a gas phase stream 404 of predominantly hydrogen, carbon dioxide and lower amounts of light hydrocarbons, an aqueous phase 412, composed of water and low levels of organic compounds, and an overhead organic phase 407. The organic phase 407 is split into three streams to provide (1) reflux back into the column, stream 406, (2) net product, stream 407, and (3) recycle stream 408, which is then recycled to provide the second reactant. In this configuration, the recycle stream will generally include alkenes and residual oxygenates that can be further condensed to $C_{8+}$ compounds, and alkanes that are non-reactive but which provide advantages to increase the yield of $C_{8+}$ compounds in the system.

Example 2

Figure 2:
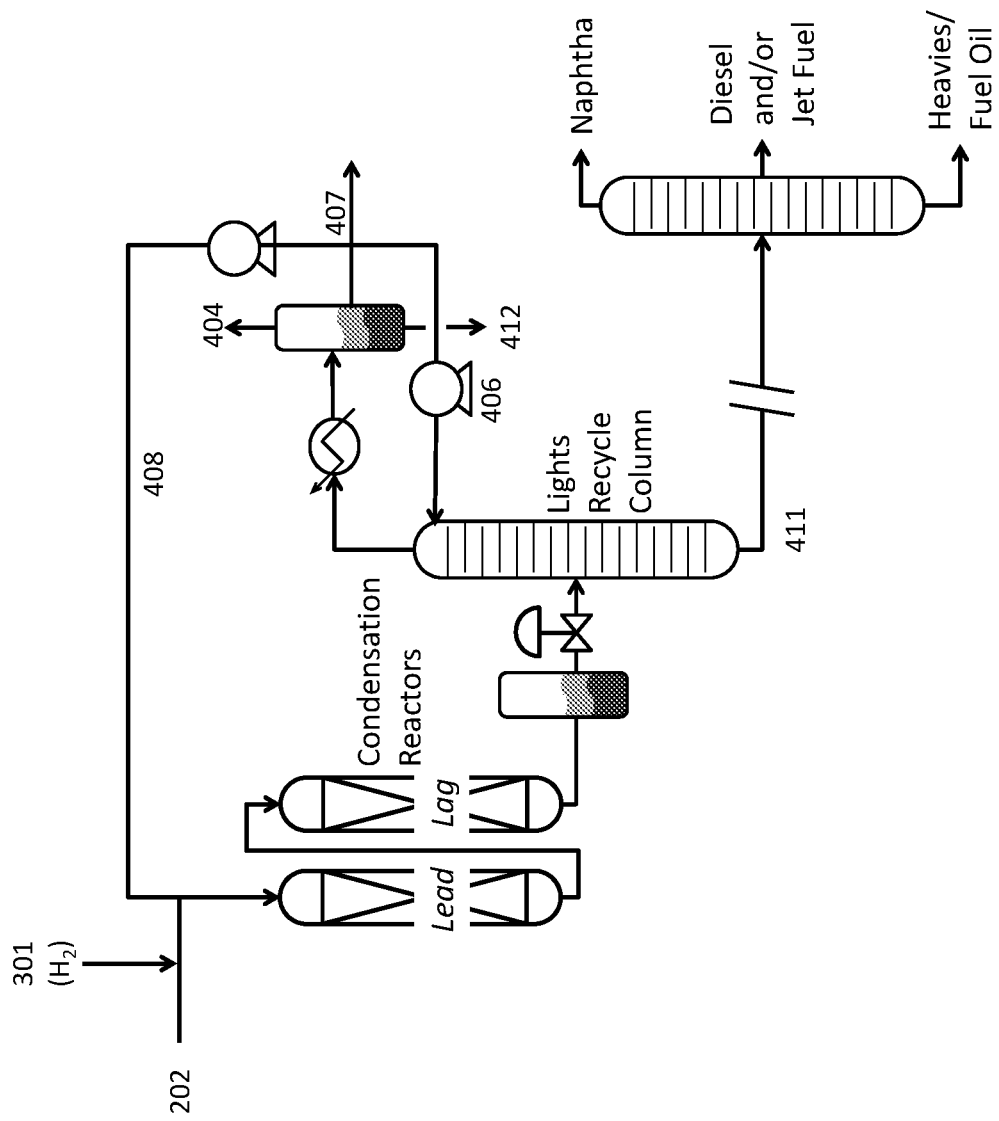
FIG. 2 is a flow diagram illustrating a reactor system for catalytically converting biomass to $C_{8+}$ compounds according to the present invention.

FIG. 2 shows a process diagram illustrating another reactor system useful in practicing the present invention. The configuration is similar to the system described in Example 1, but also includes an optional second condensation reactor in series. In this embodiment, the additional condensation reactor (as well as other additional reactors) provides further flexibility to the system—whether to allow for the use of greater amounts of catalyst, to provide temperature variations across reactors, or to employ different catalyst formulations.

Example 3

Figure 3:
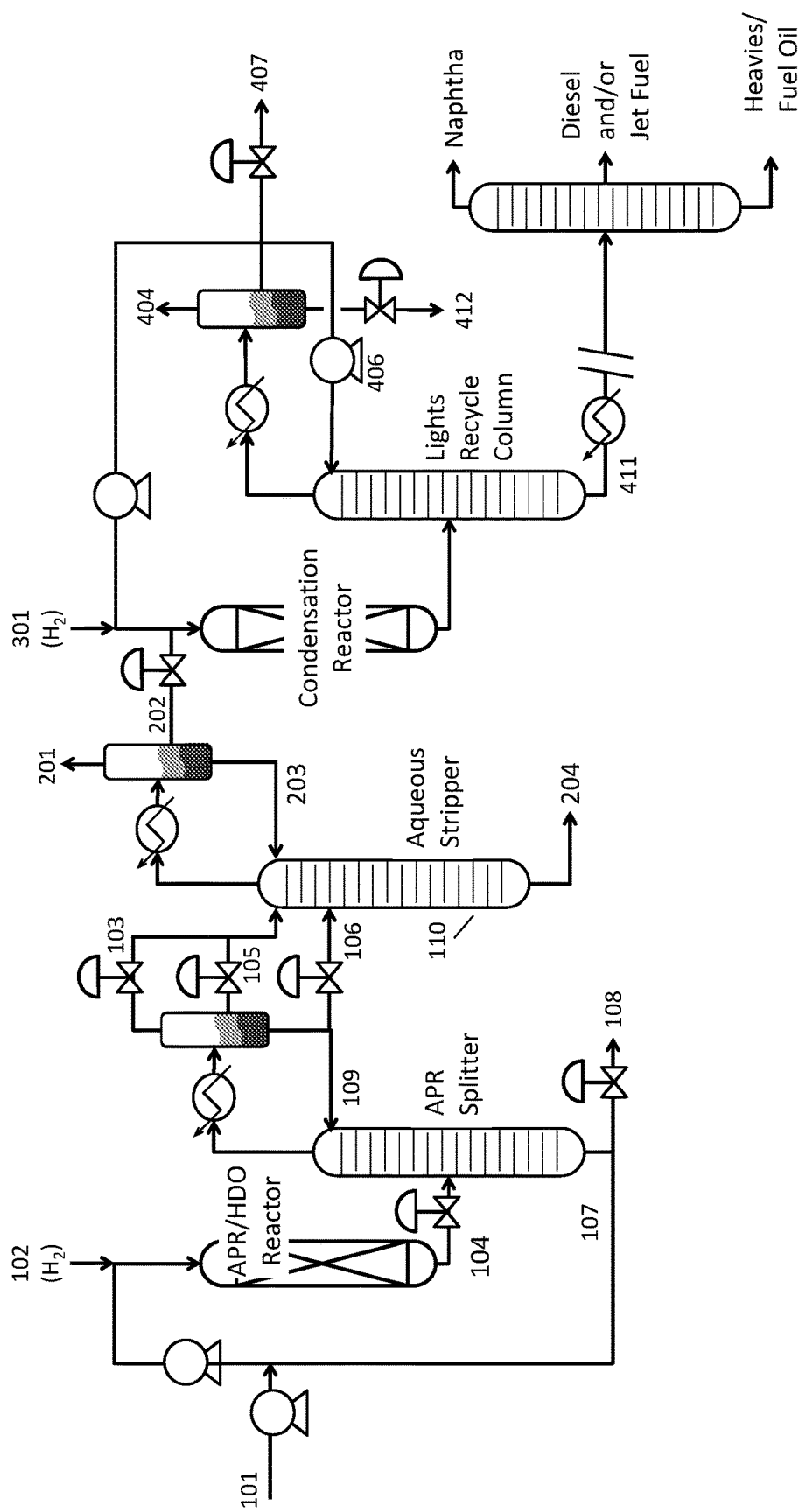
FIG. 3 is a flow diagram illustrating a reactor system for catalytically converting biomass to $C_{8+}$ compounds according to the present invention.

FIG. 3 shows a process diagram illustrating another reactor system useful in practicing the present invention. The configuration can use the same condensation reactor system as described in Examples 1 or 2 above, but also includes an optional APR/HDO reactor 104 for generating water and the first reactant, and an optional water separation unit, such as an aqueous stripper or three phase separator, for reducing the water content of the reactant stream.

Example 4

Figure 4:
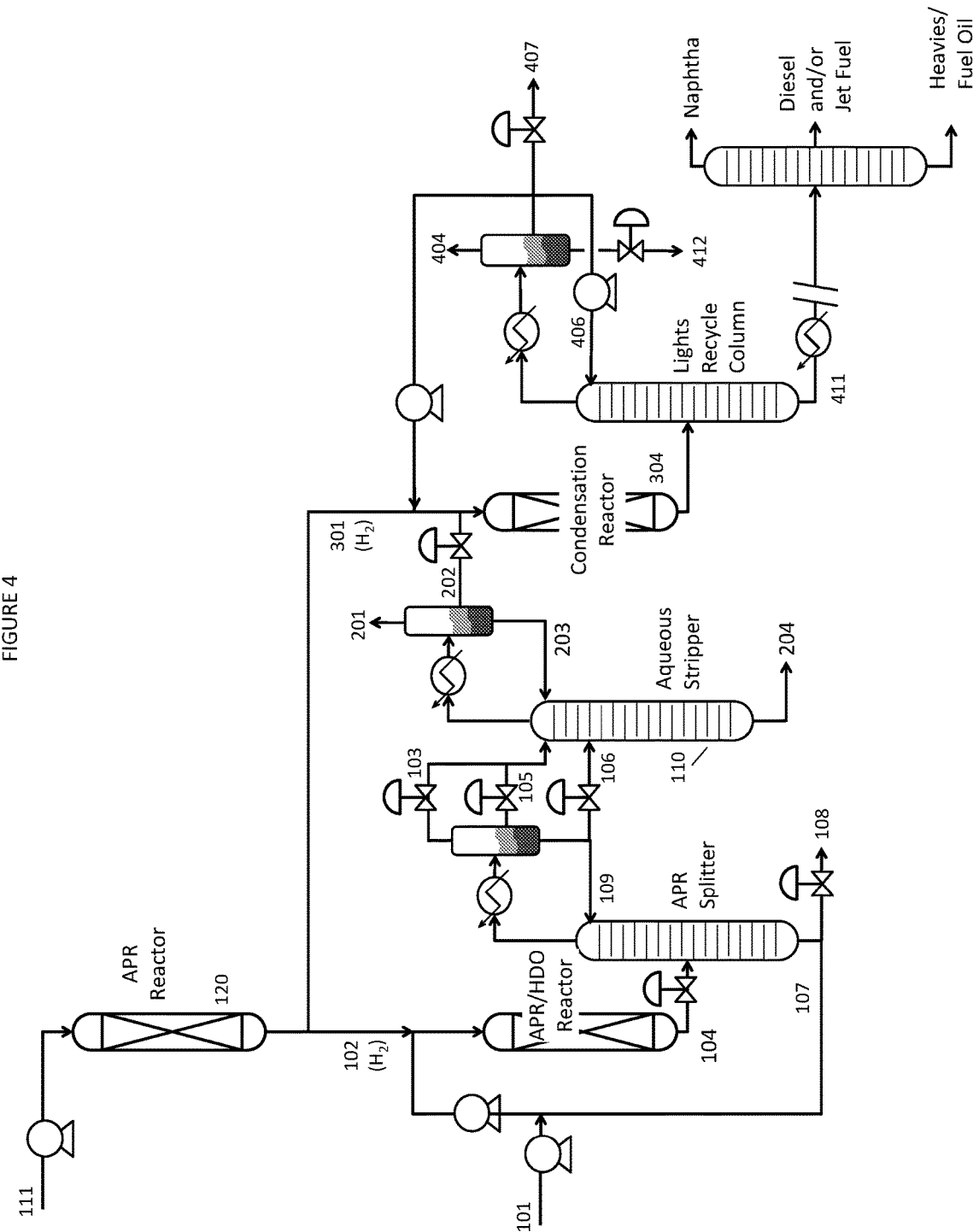
FIG. 4 is a flow diagram illustrating a reactor system for catalytically converting biomass to $C_{8+}$ compounds according to the present invention.

FIG. 4 shows a process diagram illustrating another reactor system useful in practicing the present invention. The configuration is similar to Example 3 but includes an additional APR reactor 120 for producing in situ hydrogen for use in the reactor system. In its operation, the reactor converts aqueous feed stream 111 containing water and water-soluble oxygenated hydrocarbons to a mixture of hydrogen, CO and $CO_2$ as a primary product. The hydrogen can be used to supply hydrogen consumed in the APR/HDO reactor 104 and/or condensation reactor 304.

Example 5

Figure 5:
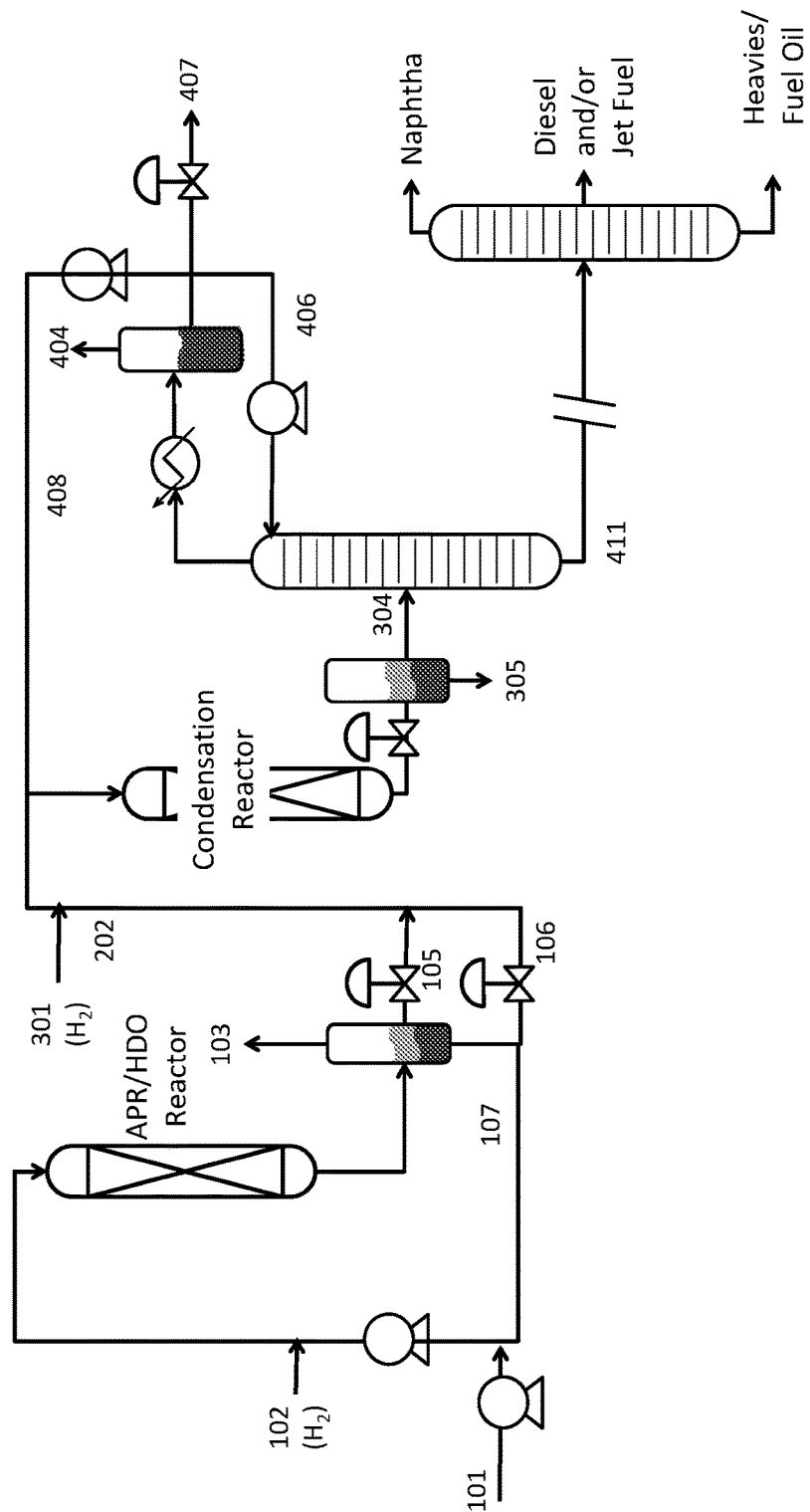
FIG. 5 is a flow diagram illustrating a reactor system for catalytically converting biomass to $C_{8+}$ compounds according to the present invention.

FIG. 5 shows a process diagram illustrating another reactor system useful in practicing the present invention. The configuration is similar to Example 3, except that no aqueous stripper is used. In this configuration, either APR/HDO organic product (stream 105) or APR/HDO aqueous product (stream 106) can be fed to the condensation reactor independently, or combined such that all liquid products are fed forward to the condensation reactor. The aqueous product stream 106 may also recycled back to the APR/HDO reactor as depicted by recycle stream 107. The condensation section can be practiced as described in Examples 1 or 2.

Analysis Techniques

Example 6

Product streams from the examples described below were analyzed as follows. The organic liquid phase was collected and analyzed using either gas chromatograph with mass spectrometry detection or flame ionization detection. Component separation was achieved using a column with a bonded 100% dimethyl polysiloxane stationary phase. Relative concentrations of individual components were estimated via peak integration and dividing by the sum of the peak areas for an entire chromatogram. Compounds were identified by comparison to standard retention times and/or comparison of mass spectra to a compiled mass spectral database. Gas phase compositions were determined by gas chromatography with a thermal conductivity detector and flame ionization or mass spectrometry detectors for other gas phase components. The aqueous fraction was analyzed by gas chromatography with and without a derivatization of the organic components using a flame ionization detector. Product yields are represented by the feed carbon present in each product fraction. The weight hourly space velocity (WHSV) was defined as the weight of feed introduced into the system per weight of catalyst per hour, and based on the weight of the oxygenated hydrocarbon feeds only, excluding water present in the feed.

APR, Deoxygenation, and Condensation

Example 7

A combined APR/deoxygenation catalyst was prepared by dissolving hexachloroplatinic acid and perrhenic acid in water and then adding the mixture to a monoclinic zirconia catalyst support (Nor Pro Saint-Gobain, Product code SZ31164, with particle sizes restricted to those that were maintained on a 14 mesh screen after passing through an 10 mesh screen) using an incipient wetness technique to target a platinum loading of 1.8% and a rhenium loading of 6.3% on the catalyst after subsequent decomposition of the metal precursors. The preparation was dried overnight in a vacuum oven and subsequently calcined in a stream of flowing air at 400° C.

Example 8

Corn syrup (43 DE) was converted to an oxygenate stream (first reactant) using the APR/deoxygenation catalyst described in Example 7. The corn syrup was mixed with water to provide an aqueous feedstock solution having a concentration of 60% 43DE corn syrup in water. The APR/deoxygenation reaction was performed using a one inch outside diameter tube reactor, and the analysis was completed as described in Example 6. The WHSV and reaction conditions were as described in Table 1 below.

The reaction resulted in an oxygenate product stream containing an organic phase, aqueous phase and gas phase. The composition of the organic phase is set forth in Table 1. Total mono-oxygenates included alcohols, ketones, tetrahydrofurans and cyclic mono-oxygenates. Cyclic mono-oxygenates included compounds in which the ring does not include oxygen, such as cyclopentanone and cyclohexanone.

TABLE 1

Conversion of Corn Syrup Across APR/Deoxygenation Catalyst

| Feed | | 60% 43DE Corn Syrup |
|---|---|---|
| WHSV | $wt_{feed}/(wt_{catalyst}\ hr)$ | 0.8 |
| Catalyst Inlet Temperature | ° C. | 195 |
| Catalyst Outlet Temperature | ° C. | 265 |
| Pressure | psig | 1050 |
| $H_2$ Co-feed | $mol_{H2}/mol_{feed}$ | 3.9 |
| Gas Phase Yield | % of feed carbon | 17 |
| Aqueous Phase Yield | % of feed carbon | 23 |
| Organic Phase Yield | % of feed carbon | 60 |
| Breakdown of Organic Phase Composition | | |
| Alkanes | % of carbon in organic phase | 15.0 |
| Total Mono-oxygenates | % of carbon in organic phase | 75.7 |
| Alcohols | % of carbon in organic phase | 40.1 |
| Ketones | % of carbon in organic phase | 11.4 |
| Cyclic Ethers | % of carbon in organic phase | 19.3 |
| Cyclic Monooxygenates | % of carbon in organic phase | 5.0 |
| Organic Acids | % of carbon in organic phase | 6.9 |
| Total $C_{7-}$ | % of carbon in organic phase | 99.0 |

Example 9

An acidic condensation catalyst was prepared by dissolving copper nitrate in water and then adding the mixture to a tungstated zirconia catalyst support (Nor Pro Saint-Gobain, Product code SZ31164, with particle sizes restricted to those that were maintained on a 60 mesh screen after passing through an 18 mesh screen) using an incipient wetness technique to target a copper loading of 10% on the catalyst after subsequent decomposition of the metal precursors. The preparation was dried overnight in a vacuum oven at 100° C. and subsequently calcined in a stream of flowing air at 400° C.

Example 10

The oxygenate stream described in Example 8 was used as a first reactant and fed over the condensation catalyst described in Example 9 using the process configuration illustrated in FIG. 1. The WHSV, reaction conditions, and light recycle ratio (ratio of second reactant) were as described in Table 2 below. The study was conducted using a one inch outside diameter tube reactor, with the condensation catalyst reduced at 400° C. under flowing hydrogen prior to its use. The $H_2$ co-feed, light recycle ratio, and heavy fraction yield were based on the first reactant stream 202 produced by the APR/HDO system described in Example 8.

A product stream was produced containing a heavy fraction and a lighter fraction. The composition of the heavy fraction is shown in Table 3. Hydrocarbons describe compounds without oxygen, and include alkanes, cycloalkanes, alkenes, cycloalkenes, and aryls. Mono-oxygenates include alcohols, ketones, cyclic ethers, and cyclic ketones. $C_{8+}$ compounds contain continuous carbon chain lengths of 8 or greater. The exception to this is the di-oxygenate category, which contain esters that do not have continuous carbon backbones. Esters would not retain their chain lengths if hydrogenated to a finished liquid fuel. The unclassified category contains compounds that are too heavy and/or co-elute with other compounds, preventing an accurate identification from the analysis technique. An estimation of carbon number is made based on boiling point and, in general, these compounds have continuous carbon chains.

A significant portion of the first reactant stream is converted to $C_{8+}$ compounds in the condensation reactor. As shown in Table 1 above, 99% of the carbon in the first reactant stream was contained in $C_{7-}$ compounds. As shown in Table 3, greater than 94% of the heavy fraction in the product stream contained $C_{8+}$ compounds. As shown in Table 2, 42% of the feed carbon was captured in the heavy product.

TABLE 2

Condensation of Oxygenates to $C_{8+}$ Compounds

| Catalyst Formulation | | 10% $CuWO_xZO_2$ |
|---|---|---|
| WHSV | $wt_{feed}/(wt_{catalyst}$ hr) | 0.4 |
| $H_2$ Co-feed | $mol_{H2}/mol_{feed}$ | 0.2 |
| Temperature | ° C. | 300 |
| Pressure | psig | 600 |
| Light Recycle Ratio | $wt_{recycle}/wt_{feed}$ | 2.5 |
| Heavy Fraction Yield | % of feed carbon | 42 |

TABLE 3

Composition of Heavy Organic Product

| $C_{7-}$ Hydrocarbons | % of carbon in organic phase | 2.2 |
|---|---|---|
| $C_{7-}$ Mono-Oxygenates | % of carbon in organic phase | 2.7 |
| Total $C_{7-}$ | % of carbon in organic phase | 6.0 |
| $C_{8+}$ Hydrocarbons | % of carbon in organic phase | 3.4 |
| $C8_+$ Mono-oxygenates | % of carbon in organic phase | 23.3 |
| $C8_+$ Di-oxygenates | % of carbon in organic phase | 1.0 |
| $C_{8+}$ Unclassified | % of carbon in organic phase | 66.3 |
| Total $C_{8+}$ Products | % of carbon in organic phase | 94.0 |

Condensation with ZSM-5 Catalysts

Example 11

An acid condensation catalyst was prepared by dissolving an aqueous nickel nitrate solution and adding it to an alumina bound ZSM-5 zeolite preparation ($SiO_2:Al_2O_3$ 30:1, crushed 1/16" extrudates with particle sizes restricted to those that were maintained on a 60 mesh screen after passing through an 18 mesh screen) using an aqueous nickel nitrate solution and an incipient wetness technique to target a nickel loading of 1.0 weight %. The preparation was dried overnight in a vacuum oven and subsequently calcined in a stream of flowing air at 400° C. A second metal was added by dissolving ruthenium nitrate in water and adding it to the catalyst using an incipient wetness technique to target a ruthenium loading of 0.5 weight %. The preparation was dried overnight in a vacuum oven and subsequently calcined in a stream of flowing air at 400° C.

Example 12

An acid condensation catalyst was prepared by dissolving copper nitrate in water and then adding it to an alumina bound ZSM-5 zeolite preparation ($SiO_2:Al_2O_3$ 30:1, crushed 1/16" extrudates with particle sizes restricted to those that were maintained on a 60 mesh screen after passing through an 18 mesh screen) using an incipient wetness technique to target a copper loading of 5.0 weight %. The preparation was dried overnight in a vacuum oven and subsequently calcined in a stream of flowing air at 400° C.

Example 13

The oxygenate stream described in Example 8 was fed over the acid condensation catalysts described in Examples 10 and 11, as well as an alumina bound ZSM-5 zeolite preparation ($SiO_2:Al_2O_3$ 30:1, crushed 1/16" extrudates with particle sizes restricted to those that were maintained on a 60 mesh screen after passing through an 18 mesh screen). The conversion was conducted using the process configuration illustrated in FIG. 2. The "lead" and "lag" reactors contained the catalyst formulations as listed in Table 4. Each catalyst was reduced at 400° C. under flowing hydrogen prior to use. The WHSV, reaction conditions, and light recycle ratio (ratio of second reactant) were as described in Table 4 below. The study was conducted using a one inch outside diameter tube reactor, with the condensation catalysts reduced at 400° C. under flowing hydrogen prior to its use. The $H_2$ co-feed, light recycle ratio, and heavy fraction yield were based on the incoming feed in the first reactant stream 202.

A heavy organic fraction was collected and analyzed as described in Example 6. Experiments B, C and D showed significant levels of condensation for a variety of metals impregnated on ZSM-5. Nickel/ruthenium, no metals, and copper catalysts were run in each combination, and resulted in a yield of 70-71% $C_{8+}$ compounds in the heavy fraction of the product stream. The first reactant used as a feedstock contained <1% $C_{8+}$ compounds at the inlet.

TABLE 4

Condensation of Oxygenates to $C_{8+}$ Compounds

| | | Experiment | | |
|---|---|---|---|---|
| | | B | C | D |
| Catalyst Composition | | Lead: CuiZSM-5 Lag: ZSM-5 | Lead: ZSM-5 Lag: Ni/ RuZSM-5 | Lead: Ni/RuZSM-5 Lag: CuZSM-5 |
| WHSV | $wt_{feed}/(wt_{catalyst}$ hr) | 0.5 | 0.5 | 0.5 |
| H2 Co-feed | $mol_{H2}/mol_{feed}$ | 0.5 | 0.5 | 0.5 |
| Catalyst Inlet Temperature | ° C. | 260 | 260 | 260 |
| Catalyst Outlet Temperature | ° C. | 310 | 310 | 310 |
| Pressure | psig | 1000 | 1000 | 1000 |
| Light Recycle Ratio | $wt_{recycle}/wt_{feed}$ | 2.5 | 2.5 | 2.5 |
| Heavy Fraction Yield | % of feed carbon | 70 | 71 | 71 |

The composition of the second reactant light recycle stream for Experiments B, C, and D is shown in Table 5. The majority of the stream is composed of alkanes that are non-reactive but which provide advantages to increase the yield of $C_{8+}$ compounds in the system. The majority of the hydrocarbons and oxygenated hydrocarbon in the stream are in the undesired $C_{7-}$ carbon range.

TABLE 5

Composition of Light Organic Recycle

|  |  | Experiment B | Experiment C | Experiment D |
|---|---|---|---|---|
| Alkanes | % of carbon in organic phase | 60.7 | 60.4 | 61.4 |
| Cyclo-Alkanes | % of carbon in organic phase | 6.5 | 7.3 | 7.3 |
| Alkenes | % of carbon in organic phase | 6.1 | 11.9 | 9.8 |
| Total Mono-oxygenates | % of carbon in organic phase | 17.5 | 13.7 | 12.1 |
| Alcohols | % of carbon in organic phase | 0.0 | 0.5 | 0.2 |
| Ketones | % of carbon in organic phase | 17.0 | 12.3 | 10.7 |
| Cyclic Ethers | % of carbon in organic phase | 0.0 | 0.1 | 0.1 |
| Cyclic Monooxygenates | % of carbon in organic phase | 0.5 | 0.8 | 1.1 |
| Organic Acids | % of carbon in organic phase | 0.5 | 1.2 | 1.2 |
| $C_{7-}$ Components | % of carbon in organic phase | 82.6 | 87.4 | 85.9 |

Example 14

An acidic condensation catalyst was prepared by dissolving an aqueous nickel nitrate solution and adding it to an alumina bound ZSM-5 zeolite preparation ($SiO_2$:$Al_2O_3$ 30:1, crushed 1/16" extrudates with particle sizes restricted to those that were maintained on a 60 mesh screen after passing through an 18 mesh screen) using an incipient wetness technique to target a nickel loading of 1.0 weight %. The preparation was dried overnight in a vacuum oven and subsequently calcined in a stream of flowing air at 400° C.

Example 15

An acidic condensation catalyst was prepared by dissolving copper nitrate in water and adding it to an alumina bound mordenite preparation (H-form, crushed 1/16" extrudates with particle sizes restricted to those that were maintained on a 60 mesh screen after passing through an 18 mesh screen) using an incipient wetness technique to target a copper loading of 5.0 weight %. The preparation was dried overnight in a vacuum oven and subsequently calcined in a stream of flowing air at 400° C.

Example 16

An acidic condensation catalyst was prepared by dissolving copper nitrate in water and adding it to a tungstated zirconia catalyst support (Nor Pro Saint-Gobain, Product code SZ31164, with particle sizes restricted to those that were maintained on a 60 mesh screen after passing through an 18 mesh screen) using an incipient wetness technique to target a copper loading of 5% on the catalyst after subsequent decomposition of the metal precursors. The preparation was dried overnight in a vacuum oven at 100° C. and subsequently calcined in a stream of flowing air at 400° C.

Example 17

The oxygenate stream (first reactant) described in Example 8 was fed over the catalysts described in Examples 14, 15 and 16 using the process configuration illustrated in FIG. 2. The same catalyst was installed in both the lead and lag reactor, and reduced at 400° C. under flowing hydrogen prior to use. The WHSV, reaction conditions, and light recycle ratio (ratio of second reactant) were as described in Table 6. The study was conducted using a one inch outside diameter tube reactor, with the condensation catalysts reduced at 400° C. under flowing hydrogen prior to its use. The $H_2$ co-feed, light recycle ratio, and heavy fraction yield were based on the incoming feed in first reactant stream 202.

A heavy organic fraction was collected and analyzed as described in Example 6. Table 7 shows the organic product yields and composition. Component classifications are the same as described in Example 10. Experiments E, F, and G show that a variety of acidic supports provide good yields to $C_{8+}$ products. The ZSM-5, Mordenite, and tungstated zirconia supports promoted condensation reactions, with the ZSM-5 and tungstated zirconia performing best with a carbon yield of 68% and 70% of the feed carbon in the heavy product fraction, respectively. As shown in Table 7, 96% or more of the carbon in the heavy product can be found in the $C_{8+}$ compounds for each experiment.

TABLE 6

Condensation of Oxygenates to $C_{8+}$ Compounds

|  |  | Experiment E | Experiment F | Experiment G |
|---|---|---|---|---|
| Catalyst Composition | Example No. | 14 | 15 | 16 |
| WHSV | $wt_{feed}/(wt_{catalyst}$ hr) | 0.5 | 0.5 | 0.3 |
| H2 Co-feed | $mol_{H2}/mol_{feed}$ | 0.4 | 0.4 | 0.4 |
| Catalyst Inlet Temperature | ° C. | 260 | 260 | 260 |
| Catalyst Outlet Temperature | ° C. | 310 | 310 | 310 |
| Pressure | psig | 1000 | 1000 | 1000 |
| Light Recycle Ratio | $wt_{recycle}/wt_{feed}$ | 2.5 | 2.5 | 2.5 |
| Heavy Fraction Yield | % of feed carbon | 68 | 57 | 70 |

TABLE 7

Composition of Heavy Organic Product

|  |  | Experiment E | Experiment F | Experiment G |
|---|---|---|---|---|
| $C_{7-}$ Hydrocarbons | % of carbon in organic phase | 1.3 | 1.0 | 1.3 |
| $C_{7-}$ Mono-Oxygenates | % of carbon in organic phase | 2.1 | 0.6 | 0.0 |
| Total $C_{7-}$ | % of carbon in organic phase | 4.0 | 2.0 | 1.3 |
| $C_{8+}$ Hydrocarbons | % of carbon in organic phase | 42.6 | 25.0 | 13.8 |
| $C_{8+}$ Mono-oxygenates | % of carbon in organic phase | 1.8 | 3.0 | 2.7 |
| $C_{8+}$ Di-oxygenates | % of carbon in organic phase | 1.0 | 0.0 | 0.2 |
| $C_{8+}$ Unclassified | % of carbon in organic phase | 50.6 | 70.0 | 81.9 |
| Total $C_{8+}$ Products | % of carbon in organic phase | 96.0 | 98.0 | 98.7 |

Example 18

The oxygenate stream described in Example 8 was fed over the catalysts described in Example 16 using the process configuration illustrated in FIG. 2. Unlike previous examples, the aqueous phase, which contained 23% of the feed carbon, was fed to the condensation reactor as well, shown as stream 106 in FIG. 5. This makes the water content of the feed much higher. The WHSV, reaction conditions, and light recycle ratio (ratio of second reactant) were as described in Table 8 below. The study was conducted using a one inch outside diameter tube reactor, with the condensation catalysts reduced at 400° C. under flowing hydrogen prior to its use. The $H_2$ co-feed, light recycle ratio, and heavy fraction yield were based on the first reactant stream 202 produced by the APR/HDO system described in Example 8.

A heavy organic fraction was collected and analyzed as described in Example 6. Experiments H and I demonstrate the ability of the second reactant light recycle to alter the $C_{8+}$ yield. By doubling the rate of the second reactant, the yield to the heavy product was increased by 11%, even though the absolute amount of water going to the condensation catalyst was the same, shown as a flow rate in Table 8.

TABLE 8

Condensation of Oxygenates to $C_{8+}$ Carbon Chains

| | | Experiment | |
|---|---|---|---|
| | | H | I |
| Catalyst Composition | Example No. | 16 | 16 |
| WHSV | $wt_{feed}/(wt_{catalyst}$ hr) | 0.4 | 0.4 |
| H2 Co-feed | $mol_{H2}/mol_{feed}$ | 0.4 | 0.4 |
| Catalyst Inlet Temperature | ° C. | 260 | 260 |
| Catalyst Outlet Temperature | ° C. | 310 | 310 |
| Pressure | psig | 1000 | 1000 |
| Light Recycle Ratio | $wt_{recycle}/wt_{feed}$ | 0.7 | 1.4 |
| Water Concentration | % $wt_{water}$ at reactor inlet | 65 | 38 |
| Water Flowrate | g/min | 2.3 | 2.3 |
| Heavy Fraction Yield | % of feed carbon | 51 | 62 |

Example 19

An APR/Deoxygenation/Condensation catalyst was prepared by dissolving palladium nitrate and silver nitrate in water and then adding it to a tungstated zirconia catalyst support (Nor Pro Saint-Gobain, Product code SZ61143, with particle sizes restricted to those that were maintained on a 60 mesh screen after passing through an 16 mesh screen) using an incipient wetness technique to target a palladium loading of 0.5% and a silver loading of 0.5% on the catalyst after subsequent decomposition of the metal precursors. The preparation was dried overnight in a vacuum oven and subsequently calcined in a stream of flowing air at 400° C.

Example 20

The catalyst system referenced in Example 19 was used to convert 43 DE corn syrup to oxygenated intermediates and then $C_{8+}$ compounds in accordance with the present invention. The corn syrup was first mixed with water to first provide an aqueous feedstock solution having a concentration of 60% 43 DE corn syrup in water. The aqueous feedstock was then directed to an APR/HDO reactor as illustrated in FIG. 5 where it was reacted over the catalyst of Example 19 to provide a first reactant stream containing water and the desired oxygenates. The WHSV and reaction conditions were as described in Table 9. The study was conducted using a one inch outside diameter tube reactor, with the catalysts reduced at 400° C. under flowing hydrogen prior to its use.

Table 9 shows the composition of the resulting organic and aqueous phases of the first reactant stream. Total mono-oxygenates include alcohols, ketones, tetrahydrofurans and cyclic mono-oxygenates. Cyclic mono-oxygenates include compounds in which the ring does not include oxygen, such as cyclopentanone and cyclohexanone. The fraction of feed carbon contained within unknown components in the aqueous phase was determined as the difference of carbon accounted for by known, measured components and the total organic carbon. The gas phase products were not processed further.

TABLE 9

Conversion of Corn Syrup Across APR/Deoxygenation Catalyst

| Feed | | 60% 43DE Corn Syrup |
|---|---|---|
| WHSV | $wt_{feed}/(wt_{catalyst}$ hr) | 0.7 |
| Catalyst Inlet Temperature | ° C. | 205 |
| Catalyst Outlet Temperature | ° C. | 254 |
| Pressure | psig | 1050 |
| H2 Co-feed | $mol_{H2}/mol_{feed}$ | 7.9 |
| Gas Phase Yield | % of feed carbon | 3 |
| Aqueous Phase Yield | % of feed carbon | 27 |
| Organic Phase Yield | % of feed carbon | 70 |
| Breakdown of Reactor Outlet Composition | | |
| Carbon Dioxide | % of feed carbon | 2 |
| Alkanes | % of feed carbon | 2 |
| Total Mono-oxygenates | % of feed carbon | 62 |
| Alcohols | % of feed carbon | 15 |
| Ketones | % of feed carbon | 16 |
| Cyclic Ethers | % of feed carbon | 17 |
| Cyclic Monooxygenates | % of feed carbon | 15 |
| Organic Acids | % of feed carbon | 2 |
| Di-Oxygenates | % of feed carbon | 9 |
| Poly-Oxygenates | % of feed carbon | 3 |
| Unknown Aqueous | % of feed carbon | 17 |
| Total $C_{7-}$ | % of feed carbon | 66 |

The organic and aqueous phases were then processed as the first reactant according to the present invention. This first reactant stream was combined with a second reactant light recycle and fed over a second catalyst bed containing the catalyst of Example 19 configured for use as an acid condensation catalyst. The WHSV, reaction conditions, and light cycle ratio (ratio of second reactant) were as described in Table 10 below. The study was conducted using a one inch outside diameter tube reactor, with the condensation catalysts reduced at 400° C. under flowing hydrogen prior to its use. The $H_2$ co-feed, light recycle ratio, and heavy fraction yield were based on the incoming feed in first reactant stream 202.

The heavy organic phase was collected and analyzed as described in Example 6. Table 11 shows the organic product yields and composition. Experiments J and K demonstrate the importance of the second reactant light recycle for the production of $C_{8+}$ products. With all other process conditions the same, Experiment J only captured 39% of the feed carbon in the desired heavy product. With the second reactant light organic recycle (stream 408 in FIG. 1), at a ratio 1.6 times greater than the incoming feed rate (stream 202 in FIG. 1), the product yield nearly doubled to 74% of the feed carbon, while the absolute amount of water going to the condensation catalyst was the same, shown as a flow rate in Table 10. This same bed of catalyst was run with a similar feed for 11 consecutive days, and the yield to $C_{8+}$ products was stable across the duration of the experiment at 72 to 73% of the feed carbon.

TABLE 10

Condensation of Oxygenates to $C_{8+}$ Carbon Chains

| | | Experiment | | |
|---|---|---|---|---|
| | | J | K | L |
| WHSV | $wt_{feed}/(wt_{catalyst}$ hr) | 0.7 | 0.7 | 0.7 |
| H2 Co-feed | $mol_{H2}/mol_{feed}$ | 1.9 | 1.9 | 1.9 |
| Time on Stream | days | 1 | 1 | 11 |
| Temperature | ° C. | 300 | 300 | 300 |
| Pressure | psig | 900 | 900 | 900 |
| Light Recycle Ratio | $wt_{recycle}/wt_{feed}$ | 0 | 1.6 | 1.6 |
| Water Concentration | % $wt_{water}$ at reactor inlet | 61 | 23 | 23 |
| Water Flowrate | g/min | 1.7 | 1.7 | 1.7 |
| Heavy Fraction Yield | % of feed carbon | 40 | 72 | 73 |

Figure 6:
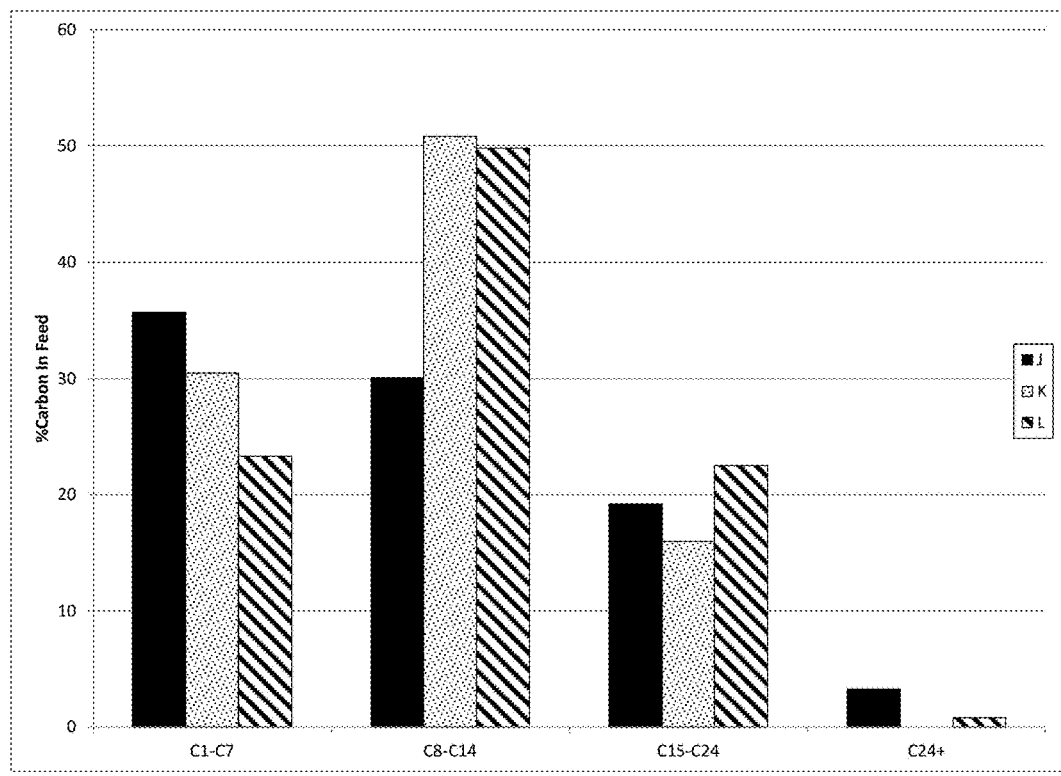
FIG. 6. is a graph showing the carbon number distribution for the product stream of Example 20.

The composition of the heavy fraction of the product stream is shown in Table 11. In either experiment the product contained >93% of the carbon in continuous carbon chains of $C_{8+}$, with Experiment L being 99.9% $C_y$. The carbon number distribution for all products coming out of the acid condensation catalyst are shown in FIG. 6. Experiment K and L with the second reactant recycle showed an increase in the yield of $C_{8+}$ compounds and decrease in the yield of the $C_{7-}$ compounds as compared to Experiment J. Even after significant time on stream, Experiment L showed improved production of $C_{8+}$ compounds, with more $C_{15-24}$ generated and less $C_{7-}$ relative to Experiment K.

TABLE 11

Composition of Heavy Fraction

| | | Experiment | | |
|---|---|---|---|---|
| | | J | K | L |
| $C_{7-}$ Hydrocarbons | % of carbon in organic phase | 2.3 | 0.0 | 0.0 |
| $C_{7-}$ Mono-Oxygenates | % of carbon in organic phase | 3.1 | 6.7 | 0.0 |
| Total $C_{7-}$ | % of carbon in organic phase | 5.4 | 6.7 | 0.1 |
| $C_{8+}$ Hydrocarbons | % of carbon in organic phase | 4.3 | 4.9 | 1.5 |
| $C_{8+}$ Mono-oxygenates | % of carbon in organic phase | 2.2 | 13.4 | 4.6 |
| $C_{8+}$ Di-oxygenates | % of carbon in organic phase | 0.0 | 0.0 | 0.0 |
| $C_{8+}$ Unclassified | % of carbon in organic phase | 86.6 | 75.0 | 93.8 |
| Total $C_{8+}$ Products | % of carbon in organic phase | 93.1 | 93.3 | 99.9 |

Figure 7:
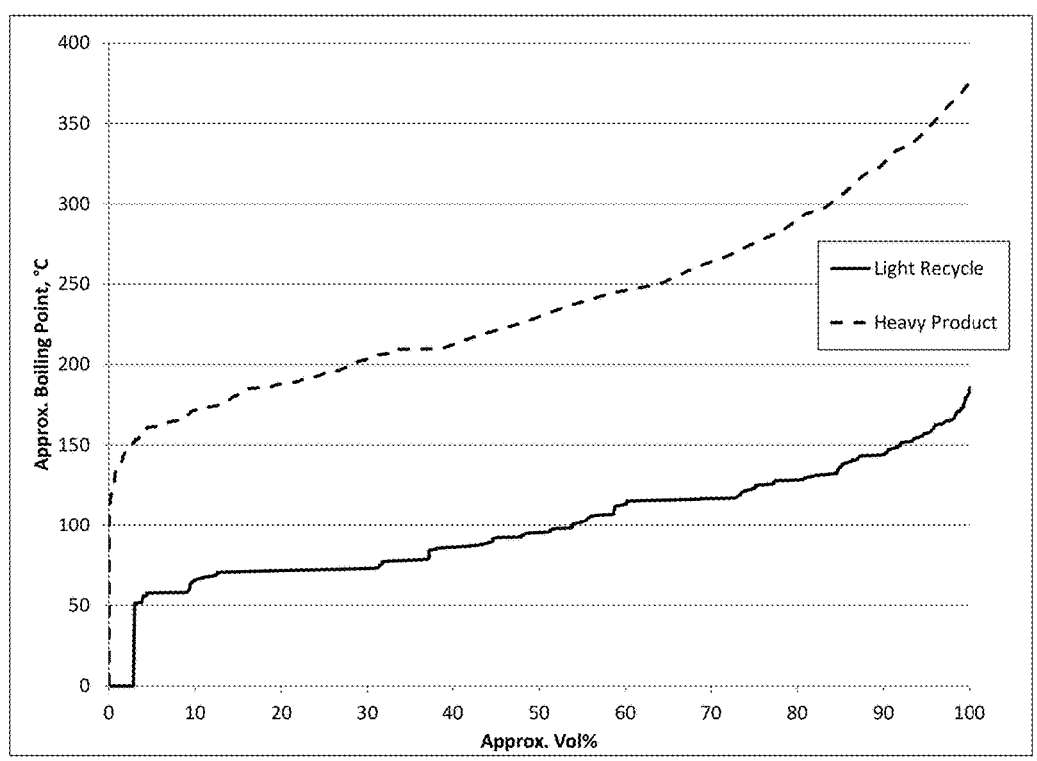
FIG. 7 is a graph showing a normal boiling point curve for both the first reactant and second reactant.

The composition of the second reactant light recycle of Experiment K and L is shown in Table 12. The majority of second reactant is composed of alkanes and cycloalkanes. These saturated hydrocarbons are mostly non-reactive over the catalyst, but provide advantages to increase the yield of $C_{8+}$ compounds in the system. The majority of the stream is in the undesired $C_{7-}$ carbon range. FIG. 7 shows a normal boiling point curve based on a simulated distillation gas chromatography method for both the light overhead recycle stream and the heavy product for Experiment L.

TABLE 12

Composition of Light Organic Recycle

| | | Experiment | |
|---|---|---|---|
| | | K | L |
| Alkanes | % of carbon in organic phase | 47.6 | 34.9 |
| Cycloalkanes | % of carbon in organic phase | 17.8 | 21.7 |
| Alkenes | % of carbon in organic phase | 0.4 | 2.3 |
| Total Mono-oxygenates | % of carbon in organic phase | 23.8 | 34.7 |
| Alcohols | % of carbon in organic phase | 0.1 | 2.6 |
| Ketones | % of carbon in organic phase | 16.4 | 25.9 |
| Cyclic Ethers | % of carbon in organic phase | 3.1 | 1.3 |
| Cyclic Monooxygenates | % of carbon in organic phase | 4.2 | 5.0 |
| Organic Acids | % of carbon in organic phase | 0.7 | 1.9 |
| C7-Components | % of carbon in organic phase | 88.1 | 82.8 |

Example 21

A reactant stream having isobutanol as the first reactant was converted to $C_{8+}$ compounds according to the present invention using the reactor system described in Example 1, but with a three phase separator as illustrated in FIGS. 2 and 5. In this instance, the first reactant stream 202 contained pure isobutanol and the second reactant recycle stream 408 contained $C_{4-}$ hydrocarbons. The acid condensation catalyst was a tungstated zirconia support (Nor Pro Saint-Gobain, Product code SZ31164, with particle sizes restricted to those that were maintained on a 14 mesh screen). The reaction was conducted in an Inconel reactor having an internal diameter of 0.87 inches, with a catalyst bed loaded to a length of 12 inches. A thermowell with an OD of 0.1875 inches was placed on the centerline of the reactor.

The bed of catalyst was heated from 25° C. to 310° C. under a hydrogen atmosphere. Once at temperature, the reactor was pressurized to 600 psig and then 100% isobutanol was fed into the reactor at a WHSV of 0.5 g isobutanol/g tungstated zirconia catalyst. To assist with pressure control, 0.08 g $H_2$/g isobutanol was fed into the process with the alcohol feedstock. Once steady state conditions were achieved, an analysis of reaction products was completed. The gas products were analyzed by means of a gas chromatograph equipped with a flame ionization detector, the aqueous phase products were analyzed for total carbon, and the organic phase components were analyzed using a gas chromatograph equipped with both flame ionization and mass spectrometry detectors.

Isobutanol was initially processed as a first reactant in the absence of a second reactant recycle stream to illustrate the impact of the second reactant. The results obtained are displayed in Table 13. To demonstrate the recycle of light intermediate products for use as a second reactant, the product stream 206 of FIG. 1 was sent forward to a distillation column (lights recycle column) to provide a light fraction containing $C_{7-}$ compounds and a heavy fraction containing $C_{8+}$ compounds. Prior to the product stream entering the column, a significant portion of the water in the 206 stream was removed by means of a three phase separator as illustrated in FIGS. 2 and 5. The 10-stage packed distillation column was pressurized to 150 psig, and a temperature profile was imposed such that the top stage was at 75° C. and the bottom stage was 170° C. The dewatered product stream entered the column at stage three. A reflux ratio of 1.2 g reflux/g isobutanol feed entered the distillation column at stage 1. Recycle of the overhead for this example was set at 2.5 g recycle/g of isobutanol. A pump boosted the pressure of the recycle stream 408 back up to 600 psig at the inlet of the reactor where it entered the catalyst bed with the isobutanol first reactant stream. Accumulation of any $C_{4-}$ material was managed by taking a light fraction stream 407 off the top of the column at a rate of 0.2 g light purge/g isobutanol. The light fraction was taken as a portion of the total overhead material where the remaining portion was the recycle stream. A high boiling point organic fraction containing $C_{8+}$ compounds was removed in the heavy fraction stream 411. Results obtained for the heavy fraction are shown in Table 14 and results obtained for the lighter fraction are shown in Table 15.

TABLE 13

Carbon Distribution for Isobutanol Conversion without Second Reactant

| | | |
|---|---|---|
| $C_{4-}$ alkenes | % of feed carbon | 53.1 |
| $C_8$ alkenes | % of feed carbon | 26.7 |
| $C_{12}$ alkenes | % of feed carbon | 0.6 |
| $C_{4-}$ alkanes | % of feed carbon | 8.8 |
| $C_{5+}$ alkanes | % of feed carbon | 1.3 |
| Total ketones | % of feed carbon | 1.3 |
| Total ethers | % of feed carbon | 1.1 |
| Total alcohols | % of feed carbon | 0.4 |
| Total dienes | % of feed carbon | 1.4 |

TABLE 14

Carbon Yield of Heavy Fraction with Second Reactant Recycle

| | | |
|---|---|---|
| $C_{4-}$ alkenes | % of feed carbon | 1.0 |
| $C_8$ alkenes | % of feed carbon | 45.0 |
| $C_{12}$ alkenes | % of feed carbon | 1.3 |
| $C_{4-}$ alkanes | % of feed carbon | 0.3 |
| $C_{5+}$ alkanes | % of feed carbon | 0.2 |
| Total ketones | % of feed carbon | 1.3 |
| Total ethers | % of feed carbon | 3.0 |
| Total alcohols | % of feed carbon | 2.8 |
| Total dienes | % of feed carbon | 2.5 |

TABLE 15

Carbon Yield of Light Fraction with Second Reactant Recycle

| | | |
|---|---|---|
| $C_{4-}$ alkenes | % of feed carbon | 35.6 |
| $C_8$ alkenes | % of feed carbon | 0 |
| $C_{12}$ alkenes | % of feed carbon | 0 |
| $C_{4-}$ alkanes | % of feed carbon | 1.8 |
| $C_{5+}$ alkanes | % of feed carbon | <0.1 |
| Total ketones | % of feed carbon | <0.1 |
| Total ethers | % of feed carbon | <0.1 |
| Total alcohols | % of feed carbon | <0.1 |
| Total dienes | % of feed carbon | <0.1 |

Example 22

The DHOG catalyst, 0.25% Pd 2% Ag on W—ZrO2, was loaded as a 16 inch packed bed in a 1 inch outer diameter Inconel reactor to examine the reactivity of propylene glycol (PG), a product of the hydrodeoxygenation, HDO, catalyst. Propylene glycol was fed to the reactor at weight hourly space velocity (WHSV) of 0.5 g PG/g catalyst per hour in a solution of approximately 50 wt % PG in water. The reactor was operated at a temperature of 300° C. and a pressure of 900 psig. Hydrogen gas was co-fed to the reactor in a ratio of approximately 1 mole $H_2$:1 mole PG fed.

The DHOG catalyst converted greater than 99% of the PG feed. The reaction resulted in a product stream containing an organic phase, aqueous phase and gas phase, and the breakdown of yields is shown in Table 16.

TABLE 16

Carbon Yields by Product Phase

| Phase | % of fed carbon |
|---|---|
| Gas | 17 |
| Aqueous | 7 |
| Organic | 74 |

Of the organic phase products, the carbon distribution is shown in Table 17, indicating greater than 90 percent of the products have carbon numbers similar to those in gasoline, jet fuel and diesel.

TABLE 17

Carbon breakdown of organic phase products

| Carbon Range | Percent of Organic Product |
|---|---|
| Light (C1-C3) | 0.3 |
| Fuel Range (C4-C20) | 91.4 |
| Heavy (C21+) | 8.3 |

The organic phase products are further classified in Table 18. The exception to this is the di-oxygenate category, which contain esters that do not have continuous carbon backbones. Esters would not retain their chain lengths if hydrogenated to a finished liquid fuel. The unclassified category contains compounds that are too heavy and/or co-elute with other compounds, preventing an accurate identification from the analysis technique. An estimation of carbon number is made based on boiling point and, in general, these compounds have continuous carbon chains.

TABLE 18

Class Breakdown of Organic Products

| Class | Percent of Organic Product |
|---|---|
| C7-Hydrocarbons | 8.0 |
| C7-Mono-oxygenates | 3.8 |
| Total C7- | 12.3 |
| C8+ Hydrocarbons | 7.5 |
| C8+ Mono-oxygenates | 13.9 |
| C8+ Di-oxygenates | 0.8 |
| C8+ Unclassified | 66.0 |
| Total C8+ Products | 87.7 |

Example 23

The DHOG catalyst, 0.25% Pd 2% Ag on W—ZrO2, was loaded as a 16 inch packed bed in a 1 inch outer diameter Inconel reactor to examine the reactivity of acetone, a product of the hydrodeoxygenation, HDO, catalyst. Acetone was fed to the reactor at weight hourly space velocity (WHSV) of 0.5 g acetone/g catalyst per hour in a solution of approximately 50 wt % acetone in water. The reactor was operated at a temperature of 300° C. and a pressure of 900 psig. Hydrogen gas was co-fed to the reactor in a ratio of approximately 0.8 mole $H_2$:1 mole acetone fed.

The DHOG catalyst converted approximately 73% of the acetone feed. The reaction resulted in a product stream containing an organic phase, aqueous phase and gas phase, and the breakdown of yields is shown in Table 19.

TABLE 19

Carbon Yields by Product Phase

| Phase | % of fed carbon |
|---|---|
| Gas | 19 |
| Aqueous | 42 |
| Organic | 36 |

The aqueous phase consisted of unreacted acetone, and also contained acetic acid. Isobutane was the primary component of the gas phase. The organic phase is characterized in Table 20, where greater than 95 percent of the organic carbon falls in the fuel range.

TABLE 20

Carbon breakdown of organic phase products

| Carbon Range | Percent of Organic Product |
|---|---|
| Light (C1-C3) | 1.0 |
| Fuel Range (C4-C20) | 95.8 |
| Heavy (C21+) | 3.2 |

Example 24

The DHOG catalyst, 0.25% Pd 2% Ag on W—ZrO2, was loaded as a 16 inch packed bed in a 1 inch outer diameter Inconel reactor to examine the reactivity of 1-hexanol, a product of the hydrodeoxygenation, HDO, catalyst. 1-hexanol was fed to the reactor at weight hourly space velocity (WHSV) of 0.5 g hexanol/g catalyst per hour in a solution of approximately 50 wt % 1-hexanol in water. The reactor was operated at a temperature of 300° C. and a pressure of 900 psig. Hydrogen gas was co-fed to the reactor in a ratio of approximately 1.3 mole $H_2$:1 mole 1-hexanol fed.

The DHOG catalyst converted greater than 99% of the 1-hexanol feed. The reaction resulted in a product stream containing an organic phase, aqueous phase and gas phase, and the breakdown of yields is shown in Table 21.

TABLE 21

Carbon Yields by Product Phase

| Phase | % of fed carbon |
|---|---|
| Gas | 2 |
| Aqueous | <0.5 |
| Organic | 98 |

Of the organic phase products, more than 65% of the product was C6, primarily n-hexane (40%) and 1-hexene (25%) and approximately 32% of the organic products were C7+.

Example 25

The DHOG catalyst, 0.25% Pd 2% Ag on W—ZrO2, was loaded as a 16 inch packed bed in a 1 inch outer diameter Inconel reactor to examine the reactivity of 1-propanol, a product of the hydrodeoxygenation, HDO, catalyst. 1-propanol was fed to the reactor at weight hourly space velocity (WHSV) of 0.5 g 1-propanol/g catalyst per hour in a solution of approximately 50 wt % 1-propanol in water. The reactor was operated at a temperature of 300° C. and a pressure of 900 psig. Hydrogen gas was co-fed to the reactor in a ratio of approximately 0.8 mole $H_2$:1 mole 1-propanol fed.

The DHOG catalyst converted greater than 98% of the 1-propanol feed. The reaction resulted in a product stream containing an organic phase, aqueous phase and gas phase, and the breakdown of yields is shown in Table 22.

TABLE 22

Carbon Yields by Product Phase

| Phase | % of fed carbon |
|---|---|
| Gas | 87 |
| Aqueous | 2 |
| Organic | 11 |

The gas phase consisted primarily of propane (57%) and propylene (25%) neither of which contributes to liquid fuel production.

Example 26

The DHOG catalyst, 0.25% Pd 2% Ag on W—ZrO2, was loaded as a 16 inch packed bed in a 1 inch outer diameter Inconel reactor to examine the reactivity of tetrahydrofuran (THF), a product of the hydrodeoxygenation, HDO, catalyst. THF was fed to the reactor at weight hourly space velocity (WHSV) of 0.5 g THF/g catalyst per hour in a solution of approximately 50 wt % THF in water. The reactor was operated at a temperature of 300° C. and a pressure of 900 psig. Hydrogen gas was co-fed to the reactor in a ratio of approximately 1 mole $H_2$:1 mole THF fed.

The DHOG catalyst converted approximately 63% of the THF feed. The reaction resulted in a product stream containing an organic phase, aqueous phase and gas phase, and the breakdown of yields is shown in Table 23.

TABLE 23

Carbon Yields by Product Phase

| Phase | % of fed carbon |
|---|---|
| Gas | 16 |
| Aqueous | 20 |
| Organic | 58 |

The organic phase is characterized in Table 24, where approximately 92 percent of the organic carbon falls in the fuel range, yet much of that carbon is the unreacted THF and other C4 components, which are of relatively low value as fuel components. A breakdown of the C4-C20 range is shown in Table 25.

TABLE 24

Carbon breakdown of organic phase products

| Carbon Range | Percent of Organic Product |
|---|---|
| Light (C1-C3) | 0.5 |
| Fuel Range (C4-C20) | 92 |
| Heavy (C21+) | 7.4 |

TABLE 25

Carbon breakdown of organic phase products

| Carbon Range | Percent of Organic Product |
|---|---|
| C4 components | 65 |
| C5-C20 components | 35 |

Example 27

The DHOG catalyst, 0.25% Pd 2% Ag on W—ZrO2, was loaded as a 16 inch packed bed in a 1 inch outer diameter Inconel reactor to examine the reactivity of a mixture of PG and 1-propanol, both products of the hydrodeoxygenation, HDO, catalyst, to determine if there was a benefit of having both compounds present rather than each component individually (Example 22 and Example 25). PG and 1-propanol were fed to the reactor at weight hourly space velocity (WHSV) of 0.25 g reactant/g catalyst per hour in a solution of approximately 25 wt % 1-propanol/25 wt % PG in water. The reactor was operated at a temperature of 300° C. and a pressure of 900 psig. Hydrogen gas was co-fed to the reactor in a ratio of approximately 0.9 mole $H_2$:1 mole reactant fed.

The DHOG catalyst converted greater than 99% of the 1-propanol and PG feed. The reaction resulted in a product stream containing an organic phase, aqueous phase and gas phase, and the breakdown of yields is shown in Table 26. The carbon balance is low due to the high concentration of propane in the gas phase, which was out of the analytical calibration range.

TABLE 2613

Carbon Yields by Product Phase

| Phase | % of fed carbon |
|---|---|
| Gas | 73 |
| Aqueous | 3 |
| Organic | 6 |

Example 28

The DHOG catalyst, 0.25% Pd 2% Ag on W—ZrO2, was loaded as a 16 inch packed bed in a 1 inch outer diameter Inconel reactor to examine the reactivity of a mixture of acetone and 1-propanol, both products of the hydrodeoxygenation, HDO, catalyst, to determine if there was a benefit of having both compounds present rather than each component individually (Example 23 and Example 25). Acetone and 1-propanol were fed to the reactor at weight hourly space velocity (WHSV) of 0.25 g reactant/g catalyst per hour in a solution of approximately 25 wt % 1-propanol/25 wt % acetone in water. The reactor was operated at a temperature of 300° C. and a pressure of 900 psig. Hydrogen gas was co-fed to the reactor in a ratio of approximately 0.8 mole $H_2$:1 mole reactant fed.

The DHOG catalyst converted greater than 99% of the 1-propanol fed and approximately 65% of the acetone fed. The reaction resulted in a product stream containing an organic phase, aqueous phase and gas phase, and the breakdown of yields is shown in Table 27. The carbon balance is low due to the high concentration of propane in the gas phase, which was out of the analytical calibration range.

TABLE 147

Carbon Yields by Product Phase

| Phase | % of fed carbon |
|---|---|
| Gas | 50 |
| Aqueous | 22 |
| Organic | 9 |

Example 29

The DHOG catalyst, 0.25% Pd 2% Ag on W—ZrO2, was loaded as a 16 inch packed bed in a 1 inch outer diameter Inconel reactor to examine the reactivity of lactic acid, a fermentation product of biomass derived carbohydrates. Lactic acid was fed to the reactor at weight hourly space velocity (WHSV) of 0.5 g lactic acid/g catalyst per hour in a solution of approximately 50 wt % lactic acid in water. The reactor was operated at a temperature of 300° C. and a pressure of 900 psig. Hydrogen gas was co-fed to the reactor in a ratio of approximately 1.2 mole $H_2$:1 mole lactic acid fed.

Figure 9:
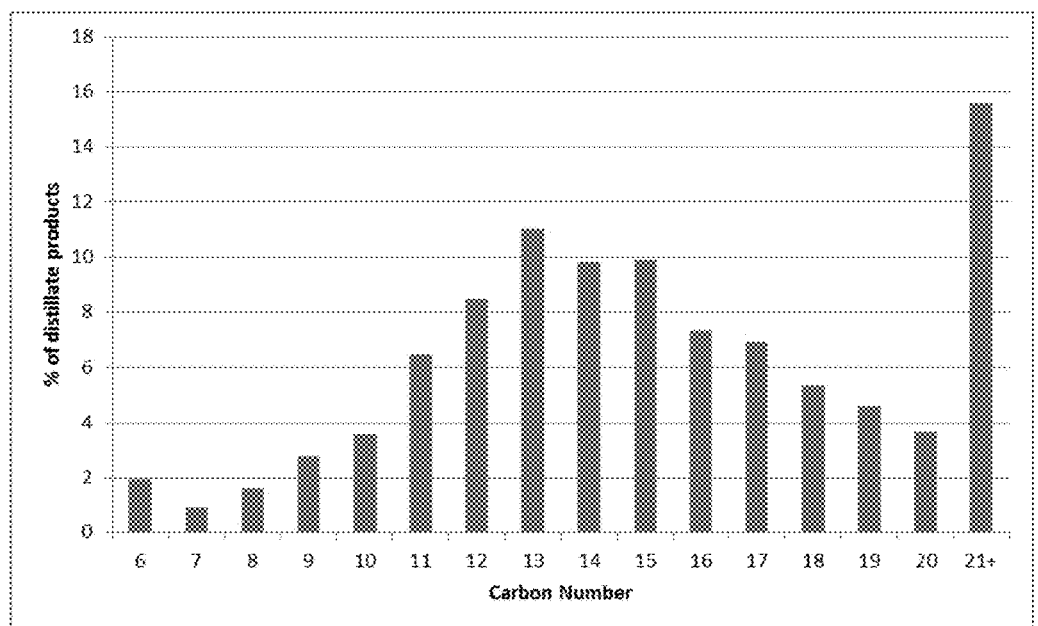
FIG. 9 is a graph showing the carbon number distribution for the distillate range product of Example 29.

The organic product of the reaction was distilled to approximately separate gasoline range products from jet, diesel, and heavier products. The carbon breakdown of the distillate range product is shown in FIG. 9.

Example 30

The DHOG catalyst, 0.25% Pd 2% Ag on ZSM-5, was loaded as a 12 inch packed bed in a 1 inch outer diameter Inconel reactor to examine the reactivity of propylene glycol (PG), a product of the hydrodeoxygenation, HDO, catalyst. Propylene glycol was fed to the reactor at weight hourly space velocity (WHSV) of 0.8 g PG/g catalyst per hour in a solution of approximately 50 wt % PG in water. The reactor was operated at a temperature of 300° C. and a pressure of 900 psig. Hydrogen gas was co-fed to the reactor in a ratio of approximately 1.4 mole $H_2$:1 mole PG fed.

The DHOG catalyst converted greater than 99% of the PG feed. The reaction resulted in a product stream containing an organic phase, aqueous phase and gas phase, and the breakdown of yields is shown in Table 28.

TABLE 28

Carbon Yields by Product Phase

| Phase | % of fed carbon |
|---|---|
| Gas | 12 |
| Aqueous | 12 |
| Organic | 75 |

Of the organic phase products, the carbon distribution is shown in Table 29, approximately 85 percent of the products have carbon numbers similar to those in gasoline, jet fuel and diesel.

TABLE 29

Carbon breakdown of organic phase products

| Carbon Range | Percent of Organic Product |
|---|---|
| Light (C1-C3) | 0.3 |
| Fuel Range (C4-C20) | 85.2 |
| Heavy (C21+) | 14.5 |

The organic phase products are further classified in Table 30. Hydrocarbons describe compounds without oxygen, and include alkanes, cycloalkanes, alkenes, cycloalkenes, and aryls. Mono-oxygenates includes alcohols, ketones, cyclic ethers, and cyclic ketones. $C_{8+}$ compounds contain continuous carbon chain lengths of 8 or greater. The exception to this is the di-oxygenate category, which contain esters that do not have continuous carbon backbones. Esters would not retain their chain lengths if hydrogenated to a finished liquid fuel. The unclassified category contains compounds that are too heavy and/or co-elute with other compounds, preventing an accurate identification from the analysis technique. An estimation of carbon number is made based on boiling point and, in general, these compounds have continuous carbon chains.

TABLE 30

Class Breakdown of Organic Products

| Class | Percent of Organic Product |
| --- | --- |
| C7-Hydrocarbons | 4.8 |
| C7-Mono-oxygenates | 5.2 |
| Total C7- | 10.4 |
| C8+ Hydrocarbons | 14.5 |
| C8+ Mono-oxygenates | 14.4 |
| C8+ Di-oxygenates | <0.01 |
| C8+ Unclassified | 60.6 |
| Total C8+ Products | 89.6 |

Example 31

A two stage catalyst system was used to convert a 60 wt % corn syrup in water feed C8+ compounds. Specifically, a deoxygenation catalyst, 8% Ni 4% Sn on t-Al2O3 was loaded in a 20 inch packed bed in a 1 inch outer diameter Inconel reactor to convert the corn syrup feed to oxygenated intermediates. The deoxygenation catalyst was operated with a temperature profile of 185-270° C. and a pressure of 1050 psig. The corn syrup solution was fed to the deoxygenation reactor at a weight hourly space velocity (WHSV) of 0.4 g corn syrup/g catalyst per hour and H2 gas was co-fed to the reactor at 1.2 molH2:mol of carbon fed. The oxygenated intermediate product is described in Table 31.

TABLE 31

Deoxygenation catalyst product breakdown

| Class | % of fed carbon |
| --- | --- |
| Paraffins | 0.61 |
| Alcohols | 4.76 |
| Ketones | 1.95 |
| Cyclic Ethers | 7.91 |
| Diols | 23.3 |
| Acids | 0.75 |
| Poly-oxygenates | 2.09 |
| Unidentified | 54.3 |

The deoxygenation product was then fed to an acid condensation catalyst, 0.25% Pd 2% Ag on W—ZrO2, which was loaded as a 10 inch packed bed in a 1 inch outer diameter Inconel reactor to convert the oxygenated intermediates to C8+ compounds. The acid condensation reaction resulted in a product stream containing an organic phase, aqueous phase and gas phase, and the breakdown of yields is shown in Table 32.

TABLE 32

Carbon Yields by Product Phase

| Phase | % of fed carbon |
| --- | --- |
| Gas | 19 |
| Aqueous | 8 |
| Organic | 71 |

Of the organic phase products, the carbon distribution is shown in Table 33 approximately 90 percent of the products have carbon numbers similar to those in gasoline, jet fuel and diesel.

TABLE 33

Carbon breakdown of organic phase products

| Carbon Range | Percent of Organic Product |
| --- | --- |
| Light (C1-C3) | 0.2 |
| Fuel Range (C4-C20) | 90.5 |
| Heavy (C21+) | 9.3 |

The organic phase products are further classified in Table 34. Hydrocarbons describe compounds without oxygen, and include alkanes, cycloalkanes, alkenes, cycloalkenes, and aryls. Mono-oxygenates includes alcohols, ketones, cyclic ethers, and cyclic ketones. $C_{8+}$ compounds contain continuous carbon chain lengths of 8 or greater. The exception to this is the di-oxygenate category, which contain esters that do not have continuous carbon backbones. Esters would not retain their chain lengths if hydrogenated to a finished liquid fuel. The unclassified category contains compounds that are too heavy and/or co-elute with other compounds, preventing an accurate identification from the analysis technique. An estimation of carbon number is made based on boiling point and, in general, these compounds have continuous carbon chains.

TABLE 3415

Class Breakdown of Organic Products

| Class | Percent of Organic Product |
| --- | --- |
| C7-Hydrocarbons | 25.1 |
| C7-Mono-oxygenates | 4.7 |
| Total C7- | 30.2 |
| C8+ Hydrocarbons | 13.5 |
| C8+ Mono-oxygenates | 9.2 |
| C8+ Di-oxygenates | 0.2 |
| C8+ Unclassified | 46.8 |
| Total C8+ Products | 69.8 |

We claim:

1. A method of making $C_{12+}$ compounds comprising:
(i) providing a first reactant stream comprising a plurality of molecules having a general formula $C_xH_yO_z$ and a first reactant average oxygen to carbon ratio of between 0.08 and 0.75 and wherein x=2-12 carbon atoms and z=1-3 oxygen atoms, the first reactant comprising at least one member selected from the group consisting of a ketone, an alcohol, an aldehyde, a cyclic ether, a carboxylic acid, a diol, a hydroxyketone, a lactone, a triol, and mixtures thereof;

(ii) providing a second reactant stream comprising a plurality of molecules having a general formula $C_pH_rO_s$ and a second reactant average oxygen to carbon ratio of 0.2 or less and wherein p=2-7 carbon atoms and s=0-1 oxygen atoms, the second reactant stream comprising one or more mono-oxygenated hydrocarbons and at least one member selected from the group consisting of an alkane, an alkene, and mixtures thereof;

(iii) combining the first reactant stream and the second reactant stream to provide a combined reactant stream wherein, of the total number of carbon atoms in the combined reactant stream, greater than 10% are from the first reactant stream and greater than 10% are from the second reactant stream;

(iv) catalytically reacting the combined reactant stream with hydrogen in the presence of an acid condensation catalyst to produce a product stream comprising water and (1) a plurality of $C_{12+}$ compounds selected from the group consisting of $C_{12+}$ alkanes, $C_{12+}$ alkenes, $C_{12+}$ cycloalkanes, $C_{12+}$ cycloalkenes, $C_{12+}$ alcohols, $C_{12+}$ ketones, an aryl, a fused aryl, an oxygenated aryl, an oxygenated fused aryl, and a mixture thereof, and (2) a plurality of $C_{7-}$ compounds having 3 to 7 carbon atoms and 0 to 2 oxygen atoms, wherein the acid condensation catalyst comprises an acidic support or a heterogeneous acid catalyst comprising a metal selected from the group consisting of Pd, Pt, Cu, Co, Ru, Cr, Ni, Ag, an alloy thereof, and a combination thereof;

(v) separating from the product stream one of a first plurality of $C_{12-24}$ compounds suitable for blending into a diesel fuel and a second plurality of $C_{25+}$ compounds suited for blending into a heavy oil; and (vi) recycling a portion of the $C_{7-}$ compounds to form at least in part the second reactant stream and wherein water is removed from the product stream prior to recycling the $C_{7-}$ compounds to form in part the second reactant stream.

2. The method of claim 1, wherein the combined reactant stream further comprises a third reactant stream comprising a plurality of molecules having a general formula $C_jH_kO_m$ and a third reactant stream average oxygen to carbon ratio of between 0.14 and 0.67 and wherein j=3-7 carbon atoms and m=1-2 oxygen atoms.

3. The method of claim 1, wherein the $C_{7-}$ compounds comprise a mixture of (i) alkanes and/or alkenes and (ii) at least one member selected from the group consisting of a ketone, an alcohol, an aldehyde, a cyclic ether, a diol, a hydroxyketone, a lactone, and mixtures thereof.

4. The method of claim 1, wherein the acidic support is selected from the group consisting of an aluminosilicate, a tungstated aluminosilicate, a silica- alumina phosphate, an aluminum phosphate, an amorphous silica alumina, an acidic alumina, a phosphate alumina, a tungstated alumina, a zirconia, a tungstated zirconia, a tungstated silica, a tungstated titania, a tungstated phosphate, niobia, an acid modified resin, a zeolite, a heteropolyacid, a tungstated heteropolyacid, and combinations thereof.

5. The method of claim 1, wherein the heterogeneous acid catalyst further comprises a support selected from the group consisting of carbon, silica, alumina, zirconia, titania, vanadia, kieselguhr, hydroxyapatite, chromia, niobia, mixtures thereof, and combinations thereof.

6. The method of claim 1, wherein the acid condensation catalyst further comprises a modifier selected from the group consisting of Cu, Ag, Au, Ru, Pd, Ni, Co, Ga, In, Cr, Mo, W, Sn, Nb, Ti, Zr, Ge, P, Al, alloys thereof, and combinations thereof.

7. The method of claim 1, wherein the acid condensation catalyst comprises ZSM-5 or tungstated zirconia.

8. The method of claim 7, wherein the acid condensation catalyst further comprises Pd or Cu.

9. The method of claim 8, wherein the acid condensation catalyst further comprises Ag.

10. The method of claim 1 further comprising the step of catalytically reacting at least a portion of the product stream in the presence of a finishing catalyst.

11. The method of claim 1 further comprising:
providing hydrogen, water and a water soluble oxygenated hydrocarbon comprising a $C_{2+}O_{1+}$ hydrocarbon, and
catalytically reacting the oxygenated hydrocarbon with the hydrogen in the presence of a deoxygenation catalyst to produce the first reactant stream.

12. The method of claim 11, wherein the deoxygenation catalyst comprises a support and a member selected from the group consisting of Re, Cu, Fe, Ru, Ir, Co, Rh, Pt, Pd, Ni, W, Os, Mo, Ag, Au, Sn, an alloy thereof, an alloy thereof, and a combination thereof.

13. The method of claim 12, wherein the support comprises a member selected from group consisting of a carbon, silica, alumina, zirconia, titania, vanadia, heteropolyacid, kieselguhr, hydroxyapatite, chromia, zeolite, and mixtures thereof.

14. The method of claim 12, wherein the deoxygenation catalyst comprises Ni and Sn and the support comprises theta alumina.

15. The method of claim 11, wherein the water soluble oxygenated hydrocarbon is selected from the group consisting of a starch, a carbohydrate, a polysaccharide, a disaccharide, a monosaccharide, an aldopentose, an aldohexose, a ketotetrose, a ketopentose, a ketohexose, a hemicellulose, a cellulosic derivative, a lignocellulosic derivative, and a polyol.

16. The method of claim 15, wherein the polyol is a sugar alcohol.

17. The method of claim 1, wherein the hydrogen comprises at least one of an in situ-generated $H_2$, external $H_2$, or recycled $H_2$.

18. The method of claim 17, wherein the hydrogen comprises hydrogen generated in situ by catalytically reacting in a liquid phase or vapor phase an aqueous feedstock solution comprising water and an oxygenated hydrocarbon in the presence of an aqueous phase reforming catalyst at a reforming temperature and reforming pressure.

* * * * *

UNITED STATES PATENT AND TRADEMARK OFFICE
CERTIFICATE OF CORRECTION

PATENT NO. : 9,593,054 B2  
APPLICATION NO. : 13/832376  
DATED : March 14, 2017  
INVENTOR(S) : John Kania et al.

Page 1 of 1

It is certified that error appears in the above-identified patent and that said Letters Patent is hereby corrected as shown below:

In the Specification

Column 15, Line 28, "PMO" should be --PMo--.

Column 45, Line 34, "TABLE 2613" should be --TABLE 26--.

Column 46, Line 1, "TABLE 147" should be --TABLE 27--.

Column 48, Line 41, "TABLE 3415" should be --TABLE 34--.

Signed and Sealed this  
Twenty-second Day of August, 2017

Joseph Matal  
*Performing the Functions and Duties of the  
Under Secretary of Commerce for Intellectual Property and  
Director of the United States Patent and Trademark Office*